US012630597B2

(12) United States Patent
Kwon et al.

(10) Patent No.: US 12,630,597 B2
(45) Date of Patent: *May 19, 2026

(54) GPC3 CAR-T CELL COMPOSITIONS AND METHODS OF MAKING AND USING THE SAME

(71) Applicant: EUTILEX CO., LTD., Seoul (KR)

(72) Inventors: Byoung S. Kwon, Seoul (KR); Kwanghee Kim, Seoul (KR); Jiwon Chung, Seoul (KR); Young Gyoon Chang, Seoul (KR); Bo-Rim Yi, Seoul (KR); Jungyun Lee, Seoul (KR); Seunghyun Lee, Seoul (KR); Sun-Woo Im, Seoul (KR); Jinkyung Choi, Seoul (KR); Hyuntae Son, Seoul (KR); Hye Mi Lee, Seoul (KR)

(73) Assignee: EUTILEX CO., LTD., Seoul (KR)

( * ) Notice: Subject to any disclaimer, the term of this patent is extended or adjusted under 35 U.S.C. 154(b) by 794 days.

This patent is subject to a terminal disclaimer.

(21) Appl. No.: 17/906,718

(22) PCT Filed: Mar. 18, 2021

(86) PCT No.: PCT/IB2021/052294
§ 371 (c)(1),
(2) Date: Sep. 19, 2022

(87) PCT Pub. No.: WO2021/186397
PCT Pub. Date: Sep. 23, 2021

(65) Prior Publication Data
US 2023/0146706 A1 May 11, 2023

Related U.S. Application Data

(60) Provisional application No. 63/043,237, filed on Jun. 24, 2020, provisional application No. 63/004,827, filed on Apr. 3, 2020, provisional application No. 62/991,493, filed on Mar. 18, 2020.

(51) Int. Cl.
| | |
|---|---|
| *C07K 14/47* | (2006.01) |
| *A61K 40/11* | (2025.01) |
| *A61K 40/31* | (2025.01) |
| *A61K 40/42* | (2025.01) |
| *A61P 35/00* | (2006.01) |
| *C07K 14/705* | (2006.01) |
| *C07K 14/725* | (2006.01) |
| *C07K 16/30* | (2006.01) |
| *C12N 5/0783* | (2010.01) |

(52) U.S. Cl.
CPC .......... *C07K 14/4725* (2013.01); *A61K 40/11* (2025.01); *A61K 40/31* (2025.01); *A61K 40/4261* (2025.01); *A61P 35/00* (2018.01); *C07K 14/705* (2013.01); *C07K 14/7051* (2013.01); *C07K 16/303* (2013.01); *C12N 5/0636* (2013.01); *A61K 2239/38* (2023.05);

*A61K 2239/53* (2023.05); *C07K 2317/565* (2013.01); *C07K 2317/622* (2013.01); *C07K 2319/02* (2013.01); *C07K 2319/03* (2013.01)

(58) Field of Classification Search
CPC ... A61K 40/31; A61K 2239/53; C07K 16/303
See application file for complete search history.

(56) References Cited

U.S. PATENT DOCUMENTS

| | | | | |
|---|---|---|---|---|
| 7,867,734 | B2 * | 1/2011 | Nakano | A61P 43/00 435/69.6 |
| 7,919,086 | B2 * | 4/2011 | Nakano | C07K 16/28 536/23.53 |
| 8,497,355 | B2 | 7/2013 | Igawa et al. | |
| 9,096,651 | B2 | 8/2015 | Igawa et al. | |
| 9,828,429 | B2 | 11/2017 | Igawa et al. | |
| 10,731,127 | B2 | 8/2020 | Li et al. | |
| 10,781,249 | B2 | 9/2020 | Tamada et al. | |
| 2010/0239577 | A1 | 9/2010 | Igawa et al. | |
| 2011/0076275 | A1 | 3/2011 | Igawa et al. | |
| 2011/0104157 | A1 | 5/2011 | Kinoshita et al. | |
| 2011/0245473 | A1 | 10/2011 | Igawa et al. | |
| 2013/0295612 | A1 | 11/2013 | Igawa et al. | |
| 2013/0317203 | A1 | 11/2013 | Igawa et al. | |

(Continued)

FOREIGN PATENT DOCUMENTS

| | | |
|---|---|---|
| CN | 102046200 A | 5/2011 |
| JP | 2017-529851 A | 10/2017 |

(Continued)

OTHER PUBLICATIONS

Gu, Xingjian, et al. "Development of inducible CD19-CAR T cells with a tet-on system for controlled activity and enhanced clinical safety." International journal of molecular sciences 19.11 (2018): 3455. (Year: 2018).*

(Continued)

*Primary Examiner* — Julie Wu

*Assistant Examiner* — Bryan William Heck

(74) *Attorney, Agent, or Firm* — Wood, Phillips, Katz, Clark & Mortimer

(57) ABSTRACT

Provided are CAR-T compositions that are directed to GPC3, including chimeric receptors, and engineered immune cells to GPC3. The disclosure also provides vectors, compositions, and methods of treatment using GPC3 antigen binding molecules and engineered immune cells. GPC3 CAR compositions provided herein can be used for the treatment of certain cancers.

22 Claims, 14 Drawing Sheets

Specification includes a Sequence Listing.

(56)                    References Cited

U.S. PATENT DOCUMENTS

| | | |
|---|---|---|
| 2015/0284465 A1 | 10/2015 | Igawa et al. |
| 2015/0315278 A1 | 11/2015 | Igawa et al. |
| 2016/0215261 A1 | 7/2016 | Li et al. |
| 2017/0121412 A1 | 5/2017 | Igawa et al. |
| 2017/0281683 A1 | 10/2017 | Heczey et al. |
| 2018/0142027 A1 | 5/2018 | Igawa et al. |
| 2019/0085085 A1 | 3/2019 | Igawa et al. |
| 2019/0262397 A1 | 8/2019 | Connolly et al. |
| 2019/0359698 A1 | 11/2019 | Tamada et al. |
| 2019/0367634 A1 | 12/2019 | Tamada et al. |

FOREIGN PATENT DOCUMENTS

| | | | | |
|---|---|---|---|---|
| KR | 10-2019-0101989 A | 9/2019 | | |
| WO | WO-2006046751 A1 * | 5/2006 | .............. | A61P 35/00 |
| WO | WO-2018019772 A1 * | 2/2018 | .............. | A61P 35/00 |
| WO | WO 2020/017479 A1 | 1/2020 | | |

OTHER PUBLICATIONS

International Search Report and Written Opinion issued Jun. 22, 2021 in PCT/IB2021/052294 filed on Mar. 18, 2021, 13 pages.

* cited by examiner

—△—muGC33     —●—huGC33

GPC3 CAR-T CELL COMPOSITIONS AND METHODS OF MAKING AND USING THE SAME

CROSS-REFERENCE TO RELATED APPLICATIONS

This application claims priority to U.S. Provisional Application Ser. No. 62/991,493,filed on Mar. 18, 2020; U.S. Provisional Application Ser. No. 63/004,827, filed on Apr. 3,2020; and U.S. Provisional Application Ser. No. 63/043, 237, filed on Jun. 24, 2020, each of which is incorporated herein by reference in its entirety.

AN INCORPORATION BY REFERENCE STATEMENT

The ASCII text file "Eutilex.txt" created on Nov. 3, 2025, having the size of 10,372bytes, is incorporated by reference into the specification.

BACKGROUND

Cancer remains one of the leading causes of death in the world. Recent statistics report that 13% of the world population dies from cancer. According to estimates from the International Agency for Research on Cancer (IARC), in 2012 there were 14.1 million new cancer cases and 8.2 million cancer deaths worldwide. By 2030, the global burden is expected to grow to 21.7 million new cancer cases and 13 million cancer deaths due to population growth and aging and exposure to risk factors such as smoking, unhealthy diet and physical inactivity. Further, pain and medical expenses for cancer treatment cause reduced quality of life for both cancer patients and their families.

T cells engineered with chimeric antigen receptors (CAR-T) have great therapeutic potential for treating diseases such as cancers. CAR-T therapeutics confer powerful target affinity and signaling function on T cell. However, the impressive efficacy of CAR-T therapies is frequently accompanied by severe side effects, such as cytokine release syndrome (CRS). Thus there remains an unmet need to develop CAR-T therapeutics and strategies that have reduced side effects.

SUMMARY

Provided herein are immune cells comprising a chimeric antigen receptor (CAR), wherein the CAR comprises an extracellular antigen-binding domain that binds specifically to glypican-3 (GPC3), a transmembrane domain, and an intracellular signaling domain. In some embodiments, the CAR is a single polypeptide. In some embodiments, the CAR is comprised of two polypeptides.

In some embodiments, the extracellular antigen-binding domain comprises: a light chain variable domain comprising a CDR1 comprising SEQ ID NO: 1, a CDR2 comprising SEQ ID NO: 2, and a CDR3 comprising SEQ ID NO: 3; and a heavy chain variable domain comprising a CDR1 comprising SEQ ID NO: 4, a CDR2 comprising SEQ ID NO: 5, and a CDR3 comprising SEQ ID NO: 6. In some embodiments, the light chain variable domain comprises a sequence that is at least 80% identical to SEQ ID NO: 10. In some embodiments, the light chain variable domain comprises a sequence that is at least 90% identical to SEQ ID NO: 10. In some embodiments, the light chain variable domain comprises a sequence that is at least 96% identical to SEQ ID NO: 10. In some embodiments, the heavy chain variable domain comprises a sequence that is at least 80% identical to SEQ ID NO: 8. In some embodiments, the heavy chain variable domain comprises a sequence that is at least 90% identical to SEQ ID NO: 8. In some embodiments, the heavy chain variable domain comprises a sequence that is at least 96% identical to SEQ ID NO: 8. In some embodiments, the antigen-binding domain is humanized. In some embodiments, the antigen-binding domain is human. In some embodiments, the antigen-binding domain is a scFv.

In some embodiments, the transmembrane domain comprises a transmembrane domain selected from a protein selected from the group consisting of: 4-1BB/CD137, an activating NK cell receptor, an immunoglobulin protein, B7-H3, BAFFR, BLAME (SLAMF8), BTLA, CD100 (SEMA4D), CD103, CD160 (BY55), CD18, CD19, CD19a, CD2, CD247, CD27, CD276 (B7-H3), CD28, CD29, CD3delta, CD3 epsilon, CD3 gamma, CD3 zeta, CD30, CD4, CD40, CD49a, CD49D, CD49f, CD69, CD7, CD84, CD8, CD8alpha, CD8beta, CD96 (Tactile), CD11a,CD11b, CD11c, CD11d, CDS, CEACAMI, CRT AM, cytokine receptor, DAP-10,DNAMI (CD226), Fc gamma receptor, GADS, GITR, HVEM (LIGHTR), IA4, ICAM-1,Ig alpha (CD79a), IL-2R beta, IL-2R gamma, IL-7R alpha, inducible T cell costimulator (ICOS), an integrin, ITGA4, ITGA6, ITGAD, ITGAE, ITGAL, ITGAM,ITGAX, ITGB2, ITGB7, ITGB1, KIRDS2, LAT, LFA-1, a ligand that specifically binds with CD83, LIGHT, LTBR, Ly9 (CD229), lymphocyte function-associated antigen-1 (LFA-1), an MHC class 1 molecule, NKG2C, NKG2D, NKp30, NKp44,NKp46, NKp80 (KLRF1), OX-40, PAG/Cbp, programmed death-1 (PD-1), PSGL1, SELPLG (CD162), a Signaling Lymphocytic Activation Molecule (a SLAM protein), SLAM (SLAMF1), SLAMF4 (CD244), SLAMF6 (NTB-A), SLAMF7, SLP-76, a TNF receptor protein, TNFR2, TNFSF14, a Toll ligand receptor, TRANCE/RANKL, VLA1, and VLA-6. In some embodiments, the transmembrane domain is a transmembrane domain from CD8alpha.

In some embodiments, the intracellular signaling domain comprises an intracellular signaling domain from a protein selected from the group consisting of: 4-1BB/CD137, an activating NK cell receptor, an immunoglobulin protein, B7-H3, BAFFR, BLAME (SLAMF8), BTLA, CD100 (SEMA4D), CD103, CD160 (BY55), CD18, CD19, CD19a, CD2, CD247, CD27,CD276 (B7-H3), CD28, CD29, CD3delta, CD3epsilon, CD3gamma, CD3zeta, CD30, CD4, CD40, CD49a, CD49D, CD49f, CD69, CD7, CD84, CD8, CD8alpha, CD8beta, CD96 (Tactile), CD11a, CD11b, CD11c, CD11d, CDS, CEACAMI, CRTAM, a cytokine receptor, DAP-10,DNAMI (CD226), Fc gamma receptor, GADS, GITR, HVEM (LIGHTR), IA4, ICAM-1, Ig alpha (CD79a), IL-2Rbeta, IL-2R gamma, IL-7R alpha, inducible T cell costimulator (ICOS), an integrin, ITGA4, ITGA6, ITGAD, ITGAE, ITGAL, ITGAM, ITGAX, ITGB2, ITGB7, ITGB1,KIRDS2, LAT, ligand that specifically binds with CD83, LIGHT, LTBR, Ly9 (CD229), Ly108,lymphocyte function-associated antigen-1 (LFA-1), a MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), a Signaling Lymphocytic Activation Molecules (SLAM protein), SLAM (SLAMF1), SLAMF4 (CD244), SLAMF6 (NTB-A), SLAMF7, SLP-76, a TNF receptor protein, TNFR2, TNFSF14, a Toll ligand receptor, TRANCE/RANKL, VLA1, and VLA-6, or any combination thereof. In some embodiments, the intracellular signaling domain is from 4-1BB and CD3zeta.

In some embodiments, the chimeric antigen receptor further comprises an additional antigen-binding domain. In some embodiments, the additional antigen-binding domain is a scFv. In some embodiments, the immune cell is a human immune cell. In some embodiments, the human immune cell is an autologous human immune cell. In some embodiments, the human immune cell is an allogeneic human immune cell. In some embodiments, the immune cell is a T cell. In some embodiments, the immune cell is an NK cell.

Provided herein are pharmaceutical compositions comprising any of the immune cells described herein and a pharmaceutically acceptable carrier. Provided herein are kits comprising a pharmaceutical composition, wherein the pharmaceutical composition is any of the pharmaceutical compositions described herein.

Provided herein are methods of treating a subject having a glypican-3-associated cancer, the method comprising administering to the subject any of the immune cells or pharmaceutical compositions described herein.

Provided herein are nucleic acids encoding a chimeric antigen receptor (CAR), wherein the CAR comprises: an extracellular antigen-binding domain that binds specifically to glypican-3(GPC3), a transmembrane domain, and an intracellular signaling domain.

In some embodiments, the CAR is a single polypeptide. In some embodiments, the CAR is comprised of two polypeptides.

In some embodiments, the extracellular antigen-binding domain comprises: a light chain variable domain comprising a CDR1 comprising SEQ ID NO: 1, a CDR2 comprising SEQ ID NO: 2, and a CDR3 comprising SEQ ID NO: 3; and a heavy chain variable domain comprising a CDR1 comprising SEQ ID NO: 4, a CDR2 comprising SEQ ID NO: 5, and a CDR3 comprising SEQ ID NO: 6. In some embodiments, the light chain variable domain comprises a sequence that is at least 80% identical to SEQ ID NO: 10. In some embodiments, the light chain variable domain comprises a sequence that is at least 90% identical to SEQ ID NO: 10. In some embodiments, the light chain variable domain comprises a sequence that is at least 96% identical to SEQ ID NO: 10. In some embodiments, the heavy chain variable domain comprises a sequence that is at least 80% identical to SEQ ID NO: 8. In some embodiments, the heavy chain variable domain comprises a sequence that is at least 90% identical to SEQ ID NO: 8. In some embodiments, the heavy chain variable domain comprises a sequence that is at least 96% identical to SEQ ID NO: 8. In some embodiments, the antigen-binding domain is humanized. In some embodiments, the antigen-binding domain is human. In some embodiments, the antigen-binding domain is a scFv.

In some embodiments, the transmembrane domain is a transmembrane domain selected from a protein selected from the group consisting of: 4-1BB/CD137, an activating NK cell receptor, an immunoglobulin protein, B7-H3, BAFFR, BLAME (SLAMF8), BTLA, CD100(SEMA4D), CD103, CD160 (BY55), CD18, CD19, CD19a, CD2, CD247, CD27, CD276 (B7-H3), CD28, CD29, CD3delta, CD3 epsilon, CD3 gamma, CD3 zeta, CD30, CD4, CD40, CD49a, CD49D, CD49f, CD69, CD7, CD84, CD8, CD8alpha, CD8beta, CD96 (Tactile), CD11a,CD11b, CD11c, CD11d, CDS, CEACAMI, CRT AM, cytokine receptor, DAP-10,DNAMI (CD226), Fc gamma receptor, GADS, GITR, HVEM (LIGHTR), IA4, ICAM-1,Ig alpha (CD79a), IL-2R beta, IL-2R gamma, IL-7R alpha, inducible T cell costimulator (ICOS), an integrin, ITGA4, ITGA6, ITGAD, ITGAE, ITGAL, ITGAM,ITGAX, ITGB2, ITGB7, ITGB1, KIRDS2, LAT, LFA-1, a ligand that specifically binds with CD83, LIGHT, LTBR, Ly9 (CD229), lymphocyte function-associated antigen-1 (LFA-1), an MHC class 1 molecule, NKG2C, NKG2D, NKp30, NKp44,NKp46, NKp80 (KLRF1), OX-40, PAG/Cbp, programmed death-1 (PD-1), PSGL1, SELPLG (CD162), a Signaling Lymphocytic Activation Molecule (a SLAM protein), SLAM (SLAMF1), SLAMF4 (CD244), SLAMF6 (NTB-A), SLAMF7, SLP-76, a TNF receptor protein, TNFR2, TNFSF14, a Toll ligand receptor, TRANCE/RANKL, VLA1, and VLA-6. In some embodiments, the transmembrane domain is a transmembrane domain from CD8alpha.

In some embodiments, the intracellular signaling domain comprises an intracellular signaling domain from a protein selected from the group consisting of: 4-1BB/CD137, an activating NK cell receptor, an immunoglobulin protein, B7-H3, BAFFR, BLAME (SLAMF8), BTLA, CD100 (SEMA4D), CD103, CD160 (BY55), CD18, CD19, CD19a, CD2, CD247, CD27,CD276 (B7-H3), CD28, CD29, CD3delta, CD3epsilon, CD3gamma, CD3zeta, CD30, CD4, CD40, CD49a, CD49D, CD49f, CD69, CD7, CD84, CD8, CD8alpha, CD8beta, CD96 (Tactile), CD11a, CD11b, CD11c, CD11d, CDS, CEACAMI, CRTAM, a cytokine receptor, DAP-10,DNAMI (CD226), Fc gamma receptor, GADS, GITR, HVEM (LIGHTR), IA4, ICAM-1, Ig alpha (CD79a), IL-2Rbeta, IL-2R gamma, IL-7R alpha, inducible T cell costimulator (ICOS), an integrin, ITGA4, ITGA6, ITGAD, ITGAE, ITGAL, ITGAM, ITGAX, ITGB2, ITGB7, ITGB1,KIRDS2, LAT, ligand that specifically binds with CD83, LIGHT, LTBR, Ly9 (CD229), Ly108,lymphocyte function-associated antigen-1 (LFA-1), a MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), a Signaling Lymphocytic Activation Molecules (SLAM protein), SLAM (SLAMF1), SLAMF4 (CD244), SLAMF6 (NTB-A), SLAMF7, SLP-76, a TNF receptor protein, TNFR2, TNFSF14, a Toll ligand receptor, TRANCE/RANKL, VLA1, and VLA-6, or any combination thereof. In some embodiments, the intracellular signaling domain is from 4-1BB and CD3zeta.

In some embodiments, the chimeric antigen receptor further comprises an additional antigen-binding domain. In some embodiments, the additional antigen-binding domain is an scFv.

Provided herein are vectors comprising any of the nucleic acids described herein. In some embodiments, a vector comprises a promoter operationally linked to the nucleic acid. In some embodiments, the promoter is a constitutive promoter. In some embodiments, the promoter is an inducible promoter. In some embodiments, the vector is a viral vector. In some embodiments, the viral vector is a lentiviral vector.

Provided herein are methods of producing an engineered immune cell, the method comprising: introducing any of the nucleic acids described herein into an immune cell or a vector as described herein, thereby producing the engineered immune cell. In some embodiments, after the introducing step, culturing the engineered immune cell. In some embodiments, the immune cell is a T cell. In some embodiments, the immune cell is a NK cell. In some embodiments, before the introducing step, obtaining the immune cell from a subject. In some embodiments, the method further comprises administering the engineered immune cell to the subject. In some embodiments, the subject has been diagnosed or identified as having a glypican-3-associated cancer.

Provided herein are engineered immune cells produced by any of the methods described herein. In some embodiments, a pharmaceutical composition comprises any of the engineered immune cells described herein and a pharmaceutically acceptable carrier.

Provided herein are methods of treating a glypican-3-associated cancer in a subject, the method comprising administering to the subject an engineered immune cell or a pharmaceutical composition. In some embodiments, the glypican-3-associated cancer is liver cancer. In some embodiments, the subject has previously been administered one or more additional anticancer therapies selected from the group consisting of: ionizing radiation, a chemotherapeutic agent, a therapeutic antibody, and a checkpoint inhibitor. In some embodiments, selected from the group consisting of: ionizing radiation, a chemotherapeutic agent, a therapeutic antibody, and a checkpoint inhibitor. In some embodiments, the subject has been identified or diagnosed as having the glypican-3-associated cancer.

DETAILED DESCRIPTION

Figure 1:
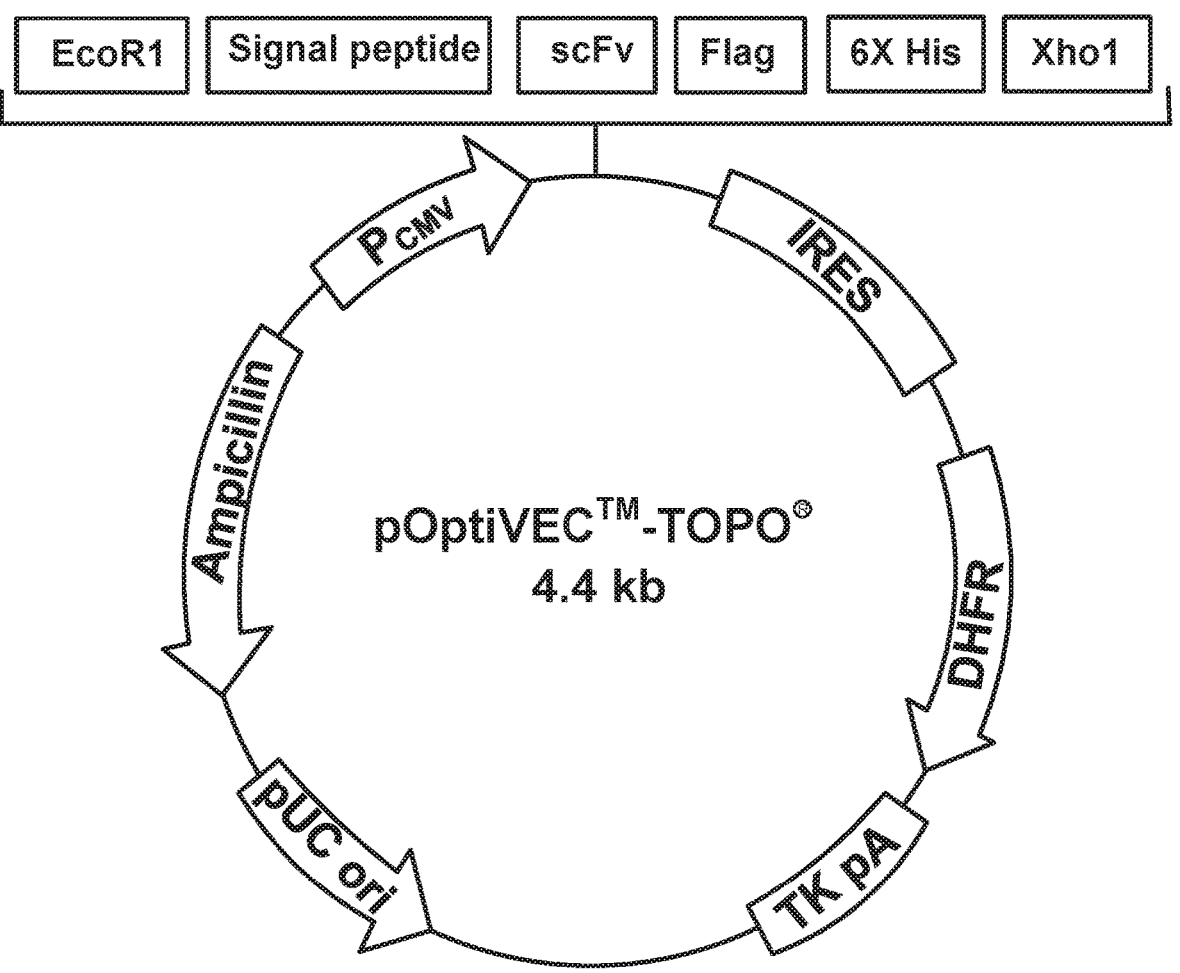
FIG. 1 show the structure of a scFv recombinant expression vector.

This disclosure describes T cells engineered with chimeric antigen receptors (CAR-T) that include a GPC3 antigen binding domain, as well as methods of making and using the same. Definitions:

About: The term "about", when used herein in reference to a value, refers to a value that is similar, in context to the referenced value. In general, those skilled in the art, familiar with the context, will appreciate the relevant degree of variance encompassed by "about" in that context. For example, in some embodiments, the term "about" may encompass a range of values that are within 25%, 20%, 19%, 18%, 17%, 16%, 15%, 14%, 13%, 12%, 11%, 10%, 9%, 8%, 7%, 6%, 5%, 4%, 3%, 2%, 1%, or less of the referred value.

Administration: As used herein, the term "administration" typically refers to the administration of a composition to a subject or system to achieve delivery of an agent that is, or is included in, the composition. Those of ordinary skill in the art will be aware of a variety of routes that may, in appropriate circumstances, be utilized for administration to a subject, for example a human. For example, in some embodiments, administration may be ocular, oral, parenteral, topical, etc. In some particular embodiments, administration may be bronchial (e.g., by bronchial instillation), buccal, dermal (which may be or comprise, for example, one or more of topical to the dermis, intradermal, interdermal, transdermal, etc.), enteral, intra-arterial, intradermal, intragastric, intramedullary, intramuscular, intranasal, intraperitoneal, intrathecal, intravenous, intraventricular, within a specific organ (e. g. intrahepatic), mucosal, nasal, oral, rectal, subcutaneous, sublingual, topical, tracheal (e.g., by intratracheal instillation), vaginal, vitreal, etc. In some embodiments, administration may involve only a single dose. In some embodiments, administration may involve application of a fixed number of doses. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

Affinity: As is known in the art, "affinity" is a measure of the tightness with a particular ligand binds to its partner. Affinities can be measured in different ways. In some embodiments, affinity is measured by a quantitative assay. In some such embodiments, binding partner concentration may be fixed to be in excess of ligand concentration so as to mimic physiological conditions. Alternatively or additionally, in some embodiments, binding partner concentration and/or ligand concentration may be varied. In some such embodiments, affinity may be compared to a reference under comparable conditions (e.g., concentrations).

Antibody agent: As used herein, the term "antibody agent" refers to an agent that specifically binds to a particular antigen. In some embodiments, the term encompasses any polypeptide or polypeptide complex that includes immunoglobulin structural elements sufficient to confer specific binding. Exemplary antibody agents include, but are not limited to monoclonal antibodies, polyclonal antibodies, and fragments thereof. In some embodiments, an antibody agent may include one or more sequence elements are humanized, primatized, chimeric, etc., as is known in the art. In many embodiments, the term "antibody agent" is used to refer to one or more of the art-known or developed constructs or formats for utilizing antibody structural and functional features in alternative presentation. For example, embodiments, an antibody agent utilized in accordance with the present invention is in a format selected from, but not limited to, intact IgA, IgG, IgE, or IgM antibodies; bi-or multi-specific antibodies (e.g., Zybodies®, etc.); antibody fragments such as Fab fragments, Fab' fragments, F (ab') 2 fragments, Fd' fragments, Fd fragments, and isolated CDRs or sets thereof; single chain Fvs; polypeptide-Fc fusions; single domain antibodies (e.g., shark single domain antibodies such as IgNAR or fragments thereof); cameloid antibodies; masked antibodies (e.g., Probodies®); Small Modular ImmunoPharmaceuticals ("SMIPs™M"); single chain or Tandem diabodies (TandAb®); VHHs; Anticalins®; Nanobodies® minibodies; BiTERs; ankyrin repeat proteins or DARPINs®; Avimers®; DARTs; TCR-like antibodies;, Adnectins®; Affilins®; Trans-bodies®; Affibodies®; TrimerX®; MicroProteins; Fynomers®, Centyrins®; and KALBITOR®s. In some embodiments, an antibody agent may lack a covalent modification (e.g., attachment of a glycan) that it would have if produced naturally. In some embodiments, an antibody agent may contain a covalent modification (e.g., attachment of a glycan, a payload [e.g., a detectable moiety, a therapeutic moiety, a catalytic moiety, etc.], or other pendant group [e.g., poly-ethylene glycol, etc.]. In many embodiments, an antibody agent is or comprises a polypeptide whose amino acid sequence includes one or more structural elements recognized by those skilled in the art as a complementarity determining region (CDR); in some embodiments an antibody agent is or comprises a polypeptide whose amino acid sequence includes at least one CDR (e.g., at least one heavy chain CDR and/or at least one light chain CDR) that is substantially identical to one found in a reference antibody. In some embodiments an included CDR is substantially identical to a reference CDR in that it is either identical in sequence or contains between 1-5 amino acid substitutions as compared with the reference CDR. In some embodiments an included CDR is substantially identical to a reference CDR in that it shows at least 85%, 86%, 87%, 88%, 89%, 90%, 91%, 92%, 93%, 94%, 95%, 96%, 97%, 98%, 99%, or 100% sequence identity with the reference CDR. In some embodiments an included CDR is substantially identical to a reference CDR in that it shows at least 96%, 96%, 97%, 98%, 99%, or 100% sequence identity with the reference CDR. In some embodiments an included CDR is substantially identical to a reference CDR in that at least one amino acid within the included CDR is deleted, added, or substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments an included CDR is substantially identical to a reference CDR in that at least one amino acid within the included CDR is substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments, an antibody agent is or comprises a polypeptide whose amino acid sequence includes structural elements recognized by those skilled in the art as an immunoglobulin variable domain. In some embodiments, an antibody agent is a polypeptide protein having a binding domain which is homologous or largely homologous to an immunoglobulin-binding domain. In some embodiments, an antibody agent is or comprises at least a portion of a chimeric antigen receptor (CAR).

Antigen: The term "antigen", as used herein, refers to an agent that binds to an antibody agent. In some embodiments, an antigen binds to an antibody agent and may or may not induce a particular physiological response in an organism. In general, an antigen may be or include any chemical entity such as, for example, a small molecule, a nucleic acid, a polypeptide, a carbohydrate, a lipid, a polymer (including biologic polymers [e.g., nucleic acid and/or amino acid polymers] and polymers other than biologic polymers [e.g., other than a nucleic acid or amino acid polymer]) etc. In some embodiments, an antigen is or comprises a polypeptide. In some embodiments, an antigen is or comprises a glycan. Those of ordinary skill in the art will appreciate that, in general, an antigen may be provided in isolated or pure form, or alternatively may be provided in crude form (e.g., together with other materials, for example in an extract such as a cellular extract or other relatively crude preparation of an antigen-containing source). In some certain embodiments, an antigen is present in a cellular context (e.g., an antigen is expressed on the surface of a cell or expressed in a cell). In some embodiments, an antigen is a recombinant antigen.

Antigen binding domain: As used herein, refers to an antibody agent or portion thereof that specifically binds to a target moiety or entity. Typically, the interaction between an antigen binding domain and its target is non-covalent. In some embodiments, a target moiety or entity can be of any chemical class including, for example, a carbohydrate, a lipid, a nucleic acid, a metal, a polypeptide, or a small molecule. In some embodiments, an antigen binding domain may be or comprise a polypeptide (or complex thereof). In some embodiments, an antigen binding domain is part of a fusion polypeptide. In some embodiments, an antigen binding domain is part of a chimeric antigen receptor (CAR).

Associated with: Two events or entities are "associated" with one another, as that term is used herein, if the presence, level, and/or form of one is correlated with that of the other. For example, a particular entity (e.g., polypeptide, genetic signature, metabolite, microbe, etc.) is considered to be associated with a particular disease, disorder, or condition, if its presence, level and/or form correlates with incidence of and/or susceptibility to the disease, disorder, or condition (e.g., across a relevant population). In some embodiments, two or more entities are physically "associated" with one another if they interact, directly or indirectly, so that they are and/or remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

Binding: It will be understood that the term "binding", as used herein, typically refers to a non-covalent association between or among two or more entities. "Direct" binding involves physical contact between entities or moieties; indirect binding involves physical interaction by way of physical contact with one or more intermediate entities. Binding between two or more entities can typically be assessed in any of a variety of contexts-including where interacting entities or moieties are studied in isolation or in the context of more complex systems (e.g., while covalently or otherwise associated with a carrier entity and/or in a biological system or cell).

Cancer: The terms "cancer", "malignancy", "neoplasm", "tumor", and "carcinoma", are used herein to refer to cells that exhibit relatively abnormal, uncontrolled, and/or autonomous growth, so that they exhibit an aberrant growth phenotype characterized by a significant loss of control of cell proliferation. In some embodiments, a tumor may be or comprise cells that are precancerous (e.g., benign), malignant, pre-metastatic, metastatic, and/or non-metastatic. The present disclosure specifically identifies certain cancers to which its teachings may be particularly relevant. In some embodiments, a relevant cancer may be characterized by a solid tumor. In some embodiments, a relevant cancer may be characterized by a hematologic tumor. In general, examples of different types of cancers known in the art include, for example, hematopoietic cancers including leukemias, lymphomas (Hodgkin's and non-Hodgkin's), myelomas and myeloproliferative disorders; sarcomas, melanomas, adenomas, carcinomas of solid tissue, squamous cell carcinomas of the mouth, throat, larynx, and lung, liver cancer, genitourinary cancers such as prostate, cervical, bladder, uterine, and endometrial cancer and renal cell carcinomas, bone cancer, pancreatic cancer, skin cancer, cutaneous or intraocular melanoma, cancer of the endocrine system, cancer of the thyroid gland, cancer of the parathyroid gland, head and neck cancers, breast cancer, gastro-intestinal cancers and nervous system cancers, benign lesions such as papillomas, and the like.

CDR: as used herein, refers to a complementarity determining region within a variable region of an antibody agent. There are three CDRs in each of the variable regions of the heavy chain and the light chain, which are designated CDR1, CDR2 and CDR3, for each of the variable regions. A "set of CDRs" or "CDR set' refers to a group of three or six CDRs that occur in either a single variable region capable of binding the antigen or the CDRs of cognate heavy and light chain variable regions capable of binding the antigen. Certain systems have been established in the art for defining CDR boundaries (e.g., Kabat, Chothia, etc.); those skilled in the art appreciate the differences between and among these systems and are capable of understanding CDR boundaries to the extent required to understand and to practice the claimed invention.

Chemotherapeutic Agent: The term "chemotherapeutic agent", has used herein has its art-understood meaning referring to one or more pro-apoptotic, cytostatic and/or cytotoxic agents, for example specifically including agents utilized and/or recommended for use in treating one or more diseases, disorders or conditions associated with undesirable cell proliferation. In many embodiments, chemotherapeutic agents are useful in the treatment of cancer. In some embodiments, a chemotherapeutic agent may be or comprise one or more alkylating agents, one or more anthracyclines, one or more cytoskeletal disruptors (e.g. microtubule targeting agents such as taxanes, maytansine and analogs thereof, of), one or more epothilones, one or more histone deacetylase inhibitors HDACs), one or more topoisomerase inhibitors (e.g., inhibitors of topoisomerase I and/or topoisomerase II), one or more kinase inhibitors, one or more nucleotide analogs or nucleotide precursor analogs, one or more peptide antibiotics, one or more platinum-based agents, one or more retinoids, one or more vinca alkaloids, and/or one or more analogs of one or more of the following (i.e., that share a relevant anti-proliferative activity). In some particular embodiments, a chemotherapeutic agent may be or comprise one or more of Actinomycin, All-trans retinoic acid, an Auiristatin, Azacitidine, Azathioprine, Bleomycin, Bortezomib, Carboplatin, Capecitabine, Cisplatin, Chlorambucil, Cyclophosphamide, Curcumin, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Irinotecan, Maytansine and/or analogs thereof (e.g. DM1) Mechlorethamine, Mercaptopurine, Methotrexate, Mitoxantrone, a Maytansinoid, Oxaliplatin, Paclitaxel, Pemetrexed, Teniposide, Tioguanine, Topotecan, Valrubicin, Vinblastine, Vincristine, Vindesine, Vinorelbine, and combinations thereof. In some embodiments, a chemotherapeutic agent may be utilized in the context of an antibody-drug conjugate. In some embodiments, a chemotherapeutic agent is one found in an antibody-drug conjugate selected from the group consisting of: hLL1-doxorubicin, hRS7-SN-38,hMN-14-SN-38, hLL2-SN-38, hA20-SN-38, hPAM4-SN-38, hLL1-SN-38, hRS7-Pro-2-P-Dox, hMN-14-Pro-2-P-Dox, hLL2-Pro-2-P-Dox, hA20-Pro-2-P-Dox, hPAM4-Pro-2-P-Dox, hLL1-Pro-2-P-Dox, P4/D10-doxorubicin, gemtuzumab ozogamicin, brentuximab vedotin, trastuzumab emtansine, inotuzumab ozogamicin, glembatumomab vedotin, SAR3419, SAR566658, BIIB015,BT062, SGN-75, SGN-CD19A, AMG-172, AMG-595, BAY-94-9343, ASG-5ME, ASG-22ME, ASG-16M8F, MDX-1203, MLN-0264, anti-PSMA ADC, RG-7450, RG-7458, RG-7593, RG- 7596, RG-7598, RG-7599, RG-7600, RG-7636, ABT-414, IMGN-853, IMGN-529, vorsetuzumab mafodotin, and lorvotuzumab mertansine.

Engineered: In general, the term "engineered" refers to the aspect of having been manipulated by the hand of man. For example, a polypeptide is considered to be "engineered" when the polypeptide sequence manipulated by the hand of man. For example, in some embodiments of the present invention, an engineered polypeptide comprises a sequence that includes one or more amino acid mutations, deletions and/or insertions that have been introduced by the hand of man into a reference polypeptide sequence. In some embodiments, an engineered polypeptide includes a polypeptide that has been fused (i.e., covalently linked) to one or more additional polypeptides by the hand of man, to form a fusion polypeptide that would not naturally occur in vivo. Comparably, a cell or organism is considered to be "engineered" if it has been manipulated so that its genetic information is altered (e.g., new genetic material not previously present has been introduced, for example by transformation, mating, somatic hybridization, transfection, transduction, or other mechanism, or previously present genetic material is altered or removed, for example by substitution or deletion mutation, or by mating protocols). As is common practice and is understood by those in the art, derivatives and/or progeny of an engineered polypeptide or cell are typically still referred to as "engineered" even though the actual manipulation was performed on a prior entity.

In vitro: The term "in vitro" as used herein refers to events that occur in an artificial environment, e.g., in a test tube or reaction vessel, in cell culture, etc., rather than within a multi-cellular organism.

In vivo: as used herein refers to events that occur within a multi-cellular organism, such as a human and a non-human animal. In the context of cell-based systems, the term may be used to refer to events that occur within a living cell (as opposed to, for example, in vitro systems).

Isolated: as used herein, refers to a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In some embodiments, as will be understood by those skilled in the art, a substance may still be considered "isolated' or even "pure", after having been combined with certain other components such as, for example, one or more carriers or excipients (e.g., buffer, solvent, water, etc.); in such embodiments, percent isolation or purity of the substance is calculated without including such carriers or excipients. To give but one example, in some embodiments, a biological polymer such as a polypeptide or polynucleotide that occurs in nature is considered to be "isolated' when, a) by virtue of its origin or source of derivation is not associated with some or all of the components that accompany it in its native state in nature; b) it is substantially free of other polypeptides or nucleic acids of the same species from the species that produces it in nature; c) is expressed by or is otherwise in association with components from a cell or other expression system that is not of the species that produces it in nature. Thus, for instance, in some embodiments, a polypeptide that is chemically synthesized or is synthesized in a cellular system different from that which produces it in nature is considered to be an "isolated' polypeptide. Alternatively or additionally, in some embodiments, a polypeptide that has been subjected to one or more purification techniques may be considered to be an "isolated' polypeptide to the extent that it has been separated from other components a) with which it is associated in nature; and/or b) with which it was associated when initially produced.

Operably linked: as used herein, refers to a juxtaposition wherein the components described are in a relationship permitting them to function in their intended manner. A control element "operably linked" to a functional element is associated in such a way that expression and/or activity of the functional element is achieved under conditions compatible with the control element. In some embodiments, "operably linked" control elements are contiguous (e.g., covalently linked) with the coding elements of interest; in some embodiments, control elements act in trans to or otherwise at the functional element of interest.

Pharmaceutical composition: As used herein, the term "pharmaceutical composition" refers to a composition in which an active agent is formulated together with one or more pharmaceutically acceptable carriers. In some embodiments, the composition is suitable for administration to a human or animal subject. In some embodiments, the active agent is present in unit dose amount appropriate for administration in a therapeutic regimen that shows a statistically significant probability of achieving a predetermined therapeutic effect when administered to a relevant population.

Polypeptide: The term "polypeptide", as used herein, generally has its art-recognized meaning of a polymer of at least three amino acids. Those of ordinary skill in the art will appreciate that the term "polypeptide" is intended to be sufficiently general as to encompass not only polypeptides having a complete sequence recited herein, but also to encompass polypeptides that represent functional fragments (i.e., fragments retaining at least one activity) of such complete polypeptides. Moreover, those of ordinary skill in the art understand that protein sequences generally tolerate some substitution without destroying activity. Thus, any polypeptide that retains activity and shares at least about 30-40% overall sequence identity, often greater than about 50%, 60%, 70%, or 80%, and further usually including at least one region of much higher identity, often greater than 90% or even 95%, 96%, 97%, 98%, or 99% in one or more highly conserved regions, usually encompassing at least 3-4 and often up to 20 or more amino acids, with another polypeptide of the same class, is encompassed within the relevant term "polypeptide" as used herein. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibody agents, antibody fragments, biologically active portions thereof, and/or characteristic portions thereof.

Prevent or prevention: as used herein when used in connection with the occurrence of a disease, disorder, and/or condition, refers to reducing the risk of developing the disease, disorder and/or condition and/or to delaying onset and/or severity of one or more characteristics or symptoms of the disease, disorder or condition. In some embodiments, prevention is assessed on a population basis such that an agent is considered to "prevent" a particular disease, disorder or condition if a statistically significant decrease in the development, frequency, and/or intensity of one or more symptoms of the disease, disorder, or condition is observed in a population susceptible to the disease, disorder, or condition.

Recombinant: as used herein, is intended to refer to polypeptides that are designed, engineered, prepared, expressed, created, manufactured, and/or or isolated by recombinant means, such as polypeptides expressed using a recombinant expression vector transfected into a host cell; polypeptides isolated from a recombinant, combinatorial human polypeptide library; polypeptides isolated from an animal (e.g., a mouse, rabbit, sheep, fish, etc.) that is transgenic for or otherwise has been manipulated to express a gene or genes, or gene components that encode and/or direct expression of the polypeptide or one or more component(s), portion(s), element(s), or domain(s) thereof; and/or polypeptides prepared, expressed, created or isolated by any other means that involves splicing or ligating selected nucleic acid sequence elements to one another, chemically synthesizing selected sequence elements, and/or otherwise generating a nucleic acid that encodes and/or directs expression of the polypeptide or one or more component(s), portion(s), element(s), or domain(s) thereof. In some embodiments, one or more of such selected sequence elements is found in nature. In some embodiments, one or more of such selected sequence elements is designed in silico. In some embodiments, one or more such selected sequence elements results from mutagenesis (e.g., in vivo or in vitro) of a known sequence element, e.g., from a natural or synthetic source such as, for example, in the germline of a source organism of interest (e.g., of a human, a mouse, etc.).

Specific binding: As used herein, the term "specific binding" refers to an ability to discriminate between possible binding partners in the environment in which binding is to occur. A binding agent that interacts with one particular target when other potential targets are present is said to "bind specifically" to the target with which it interacts. In some embodiments, specific binding is assessed by detecting or determining degree of association between the binding agent and its partner; in some embodiments, specific binding is assessed by detecting or determining degree of dissociation of a binding agent-partner complex; in some embodiments, specific binding is assessed by detecting or determining ability of the binding agent to compete an alternative interaction between its partner and another entity. In some embodiments, specific binding is assessed by performing such detections or determinations across a range of concentrations.

Subject: As used herein, the term "subject" refers an organism, typically a mammal (e.g., a human, in some embodiments including prenatal human forms). In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered.

Therapeutic agent: As used herein, the phrase "therapeutic agent" in general refers to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms. In some embodiments, an appropriate population may be defined by various criteria, such as a certain age group, gender, genetic background, preexisting clinical conditions, etc. In some embodiments, a therapeutic agent is a substance that can be used to alleviate, ameliorate, relieve, inhibit, prevent, delay onset of, reduce severity of, and/or reduce incidence of one or more symptoms or features of a disease, disorder, and/or condition. In some embodiments, a "therapeutic agent" is an agent that has been or is required to be approved by a government agency before it can be marketed for administration to humans. In some embodiments, a "therapeutic agent" is an agent for which a medical prescription is required for administration to humans.

Therapeutically Effective Amount: As used herein, the term "therapeutically effective amount" means an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, stabilizes one or more characteristics of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. For example, in some embodiments, term "therapeutically effective amount", refers to an amount which, when administered to an individual in need thereof in the context of inventive therapy, will block, stabilize, attenuate, or reverse a cancer-supportive process occurring in said individual, or will enhance or increase a cancer-suppressive process in said individual. In the context of cancer treatment, a "therapeutically effective amount" is an amount which, when administered to an individual diagnosed with a cancer, will prevent, stabilize, inhibit, or reduce the further development of cancer in the individual. A particularly preferred "therapeutically effective amount" of a composition described herein reverses (in a therapeutic treatment) the development of a malignancy such as a pancreatic carcinoma or helps achieve or prolong remission of a malignancy. A therapeutically effective amount administered to an individual to treat a cancer in that individual may be the same or different from a therapeutically effective amount administered to promote remission or inhibit metastasis. As with most cancer therapies, the therapeutic methods described herein are not to be interpreted as, restricted to, or otherwise limited to a "cure" for cancer; rather the methods of treatment are directed to the use of the described compositions to "treat" a cancer, i.e., to effect a desirable or beneficial change in the health of an individual who has cancer. Such benefits are recognized by skilled healthcare providers in the field of oncology and include, but are not limited to, a stabilization of patient condition, a decrease in tumor size (tumor regression), an improvement in vital functions (e.g., improved function of cancerous tissues or organs), a decrease or inhibition of further metastasis, a decrease in opportunistic infections, an increased survivability, a decrease in pain, improved motor function, improved cognitive function, improved feeling of energy (vitality, decreased malaise), improved feeling of well-being, restoration of normal appetite, restoration of healthy weight gain, and combinations thereof. In addition, regression of a particular tumor in an individual (e.g., as the result of treatments described herein) may also be assessed by taking samples of cancer cells from the site of a tumor such as a pancreatic adenocarcinoma (e.g., over the course of treatment) and testing the cancer cells for the level of metabolic and signaling markers to monitor the status of the cancer cells to verify at the molecular level the regression of the cancer cells to a less malignant phenotype. For example, tumor regression induced by employing the methods of this invention would be indicated by finding a decrease in any of the pro-angiogenic markers discussed above, an increase in anti-angiogenic markers described herein, the normalization (i.e., alteration toward a state found in normal individuals not suffering from cancer) of metabolic pathways, intercellular signaling pathways, or intracellular signaling pathways that exhibit abnormal activity in individuals diagnosed with cancer. Those of ordinary skill in the art will appreciate that, in some embodiments, a therapeutically effective amount may be formulated and/or administered in a single dose. In some embodiments, a therapeutically effective amount may be formulated and/or administered in a plurality of doses, for example, as part of a dosing regimen.

Variant: As used herein in the context of molecules, e.g., nucleic acids, proteins, or small molecules, the term "variant" refers to a molecule that shows significant structural identity with a reference molecule but differs structurally from the reference molecule, e.g., in the presence or absence or in the level of one or more chemical moieties as compared to the reference entity. In some embodiments, a variant also differs functionally from its reference molecule. In general, whether a particular molecule is properly considered to be a "variant" of a reference molecule is based on its degree of structural identity with the reference molecule. As will be appreciated by those skilled in the art, any biological or chemical reference molecule has certain characteristic structural elements. A variant, by definition, is a distinct molecule that shares one or more such characteristic structural elements but differs in at least one aspect from the reference molecule. To give but a few examples, a polypeptide may have a characteristic sequence element comprised of a plurality of amino acids having designated positions relative to one another in linear or three-dimensional space and/or contributing to a particular structural motif and/or biological function; a nucleic acid may have a characteristic sequence element comprised of a plurality of nucleotide residues having designated positions relative to on another in linear or three-dimensional space. In some embodiments, a variant polypeptide or nucleic acid may differ from a reference polypeptide or nucleic acid as a result of one or more differences in amino acid or nucleotide sequence. In some embodiments, a variant polypeptide or nucleic acid shows an overall sequence identity with a reference polypeptide or nucleic acid that is at least 85%, 86%, 87%, 88%, 89%, 90%, 91%, 92%, 93%, 94%, 95%, 96%, 97%, or 99%. In some embodiments, a variant polypeptide or nucleic acid does not share at least one characteristic sequence element with a reference polypeptide or nucleic acid. In some embodiments, a reference polypeptide or nucleic acid has one or more biological activities. In some embodiments, a variant polypeptide or nucleic acid shares one or more of the biological activities of the reference polypeptide or nucleic acid.

Vector: as used herein, refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "expression vectors." Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al., *Molecular Cloning: A Laboratory Manual* $2^{nd}$ ed., Cold Spring Harbor Laboratory Press, Cold Spring Harbor, N.Y. (1989)), which is incorporated herein by reference for any purpose.

Engineered Immune Cells

As used herein, "immune cells" refer to cells of the immune system which can be categorized as lymphocytes (e.g., T cells, B cells, and NK cells), neutrophils, and monocytes/macrophages. In some embodiments, the immune cell is a T cell. In some embodiments, the immune cell is an NK cell. In some embodiments, an immune cell is an engineered immune cell, which means the immune cell has been genetically modified to express a non-naturally occurring protein (e.g., a chimeric antigen receptor) or to include an exogenous nucleic acid.

The immune cells (e.g., T cells) may be modified in one or more than one manner. Immune cells (e.g., T cells) may express at least one non-natural molecule that is a receptor for an antigen that is present on the surface of one or more types of cells. In some embodiments, immune cells, include immune cells (e.g., T cells) that are not found in nature because they are engineered to comprise or express at least one synthetic molecule that is not found in nature. In specific embodiments, the immune cells (e.g., T cells) are engineered to express at least one chimeric antigen receptor (CAR), including a CAR that targets a specific tumor antigen, such as glypican-3 (GPC3). In specific embodiments, the immune cell can be a T cell, e.g., a CD4$^+$T cell, a CD8$^+$T cell, a Treg cell, a Th1 T cell, a Th2 T cell, a Th17 T cell, an unspecific T cell, or a population of T cells that comprises a combination of any of the foregoing. Immune cells (e.g., T cells) engineered with chimeric antigen receptors (CAR T cells) have great therapeutic potential for treating cancers. With a CAR, a receptor can be programmed to recognize an antigen, which when bound, activate immune cells to kill the cell expressing that antigen. Therefore, immune cells expressing CAR(s) for an antigen expressed on a tumor cell can target and kill the tumor cell. For example, recent clinical trials of a CD19-targeted CAR-transduced T cell (CD19-CAR T cell) against hematologic malignancies showed a strong effect of CAR T technology. (Kochenderfer, J. N. et al. (2010) *Blood* 116:4099-4102; Porter, D. L., et al. (2011) *N. Engl. J. Med.* 365:725-733; Grupp, S. A. et al. (2013) *N. Engl. J. Med.* 368:1509-1518;Kochenderfer, J. N. et al. (2015) *J. Clin. Oncol.* 33:540-549; Brown, C. E. et al. (2016) *N. Engl. J. Med.* 375:2561-2569). The clinical success of CAR T is attributed, at least in part, to the fusion structure of the CAR, which is made by artificially combining a high-affinity antigen-binding domain with multiple signaling domains (Maus, M. V. et al. (2014) *Blood* 123: 2625-2635; van der Stegen, S. J. et al. (2015) *Nat. Rev. Drug Discov.* 14:499-509).

CARs comprise an extracellular antigen-binding domain, a transmembrane domain and an intracellular signaling domain. In some embodiments, the extracellular antigen-binding domain comprises a single chain variable fragment (scFv) that is capable of recognizing a tumor-associated antigen, the transmembrane domain employs the transmembrane domain from molecules such as CD8 and CD28, and the intracellular signaling domain employs an immunoreceptor tyrosine-based activation motif (e.g., CD35) and the intracellular signaling domain of co-stimulatory signaling molecule (e.g., CD28, CD137, and CD137 (4-1BB)).

As used herein, "single chain variable fragment, scFv" refers to a fragment of antibody defined as a recombinant protein comprising a heavy chain variable domain (VH) and a light chain variable domain (VL) connected by a linker, which brings the two domains together into association such that an antigen-binding site is formed.

In some embodiments, the transmembrane domain is a transmembrane domain from a protein selected from 4-1BB/CD137, an activating NK cell receptor, an immunoglobulin protein, B7-H3, BAFFR, BLAME (SLAMF8), BTLA, CD100 (SEMA4D), CD103, CD160 (BY55), CD18, CD19, CD19a, CD2, CD247, CD27, CD276 (B7-H3), CD28, CD29, CD3delta, CD3epsilon, CD3 gamma, CD3 zeta, CD30, CD4, CD40, CD49a, CD49D, CD49f, CD69, CD7, CD84, CD8, CD8alpha, CD8beta, CD96 (Tactile), CD11a, CD11b, CD11c, CD11d, CDS, CEACAMI, CRT AM, cytokine receptor, DAP-10,DNAMI (CD226), Fc gamma receptor, GADS, GITR, HVEM (LIGHTR), IA4, ICAM-1, Ig alpha (CD79a), IL-2R beta, IL-2R gamma, IL-7R alpha, inducible T cell costimulator (ICOS), an integrin, ITGA4, ITGA6, ITGAD, ITGAE, ITGAL, ITGAM,ITGAX, ITGB2, ITGB7, ITGB1, KIRDS2, LAT, LFA-1, a ligand that specifically binds with CD83, LIGHT, LTBR, Ly9 (CD229), lymphocyte function-associated antigen-1 (LFA-1), an MHC class 1 molecule, NKG2C, NKG2D, NKp30, NKp44, NKp46,NKp80 (KLRF1), OX-40, PAG/Cbp, programmed death-1 (PD-1), PSGL1, SELPLG (CD162), a Signaling Lymphocytic Activation Molecule (a SLAM protein), SLAM (SLAMF1), SLAMF4(CD244), SLAMF6 (NTB-A), SLAMF7, SLP-76, a TNF receptor protein, TNFR2, TNFSF14, a Toll ligand receptor, TRANCE/RANKL, VLA1, and VLA-6.

In some embodiments, the intracellular signaling domain comprises an intracellular signaling domain from a protein selected from 4-1BB/CD137, an activating NK cell receptor, an immunoglobulin protein, B7-H3, BAFFR, BLAME (SLAMF8), BTLA, CD100 (SEMA4D), CD103, CD160 (BY55), CD18, CD19, CD19a,CD2, CD247, CD27, CD276 (B7-H3), CD28,CD29, CD3delta, CD3epsilon, CD3gamma, CD3zeta, CD30, CD4, CD40, CD49a, CD49D, CD49f, CD69, CD7, CD84, CD8,CD8alpha, CD8beta, CD96 (Tactile), CD11a, CD11b, CD11c, CD11d, CDS, CEACAMI, CRTAM, a cytokine receptor, DAP-10, DNAMI (CD226), Fc gamma receptor, GADS, GITR, HVEM (LIGHTR), IA4, ICAM-1, Ig alpha (CD79a), IL-2Rbeta, IL-2R gamma, IL-7R alpha, inducible T cell costimulator (ICOS), an integrin, ITGA4, ITGA6,ITGAD, ITGAE, ITGAL, ITGAM, ITGAX, ITGB2, ITGB7, ITGB1, KIRDS2, LAT, ligand that specifically binds with CD83, LIGHT, LTBR, Ly9 (CD229), Ly108, lymphocyte function-associated antigen-1 (LFA-1), a MHC class 1 molecule, NKG2C, NKG2D, NKp30, NKp44,NKp46, NKp80 (KLRF1), OX-40, PAG/Cbp, programmed death-1 (PD-1), PSGL1, SELPLG (CD162), a Signaling Lymphocytic Activation Molecules (SLAM protein), SLAM (SLAMF1), SLAMF4 (CD244), SLAMF6 (NTB-A), SLAMF7, SLP-76, a TNF receptor protein, TNFR2,TNFSF14, a Toll ligand receptor, TRANCE/RANKL, VLA1, and VLA-6, or any combination thereof.

In some embodiments, the chimeric antigen receptor further comprises an additional antigen-binding domain. In some embodiments, the additional antigen-binding domain is a scFv.

The immune cells, (e.g., T cells) can come from any source known in the art. For example, immune (e.g., T) cells can be differentiated in vitro from a hematopoietic stem cell population, or immune (e.g., T) cells can be obtained from a subject. T cells can be obtained from peripheral blood mononuclear cells (PBMCs), bone marrow, lymph node tissue, cord blood, thymus tissue, tissue from a site of infection, ascites, pleural effusion, spleen tissue, or tumors. In addition, immune (e.g., T) cells can be derived from one or more immune cell lines available in the art. In some embodiments, T cells can be obtained from blood collected from a subject using any number of techniques known to the skilled artisan, such as FICOLL™ separation and/or apheresis. Additional methods of isolating T cells for a T cell therapy are disclosed in U.S. Patent Publication No. 2013/0287748, which is incorporated by reference in its entirety. Other non-limiting examples can be found in International Application No. PCT/US2015/014520 (published as WO2015/120096) and in International Application No. PCT/US2016/057983 (published as WO2017/070395), each of which is herein incorporated by reference in its entirety.

In some embodiments, the immune cells are autologous T cells. In some embodiments, the immune cells are obtained from a subject that is not the patient. In some embodiments, T cells for using in a therapeutic method are syngeneic (the donor and the recipients are different but are identical twins). In some embodiments, T cells for using in a therapeutic method are allogenic (from the same species but different donor) as the recipient subject. In some embodiments, the T cells are autologous stem cells (for autologous stem cell therapy or ASCT). In some embodiments, the immune cells are non-autologous T-cells. In some embodiments, the immune cells are obtained from a healthy donor. In some embodiments, the immune cells are obtained from a patient afflicted with a cancer or a tumor.

T cells can be engineered to express, for example, chimeric antigen receptors (CARs). In some embodiments, CAR-T cells can be engineered to express an extracellular single chain variable fragment (scFv). In some embodiments, the CAR is engineered such that the costimulatory domain is expressed as a separate polypeptide chain. Exemplary CAR-T cell therapies and constructs are described in U.S. Patent Publication Nos. 2013/0287748,2014/0227237, 2014/0099309, and 2014/0050708, which are herein incorporated by reference in their entirety.

GPC3

Glypican-3 (GPC3) is a cell surface protein encoded by the GPC3 gene in humans and an oncofetal antigen re-expressed in a high frequency of neoplastic hepatocytes. GPC3 is highly expressed in fetal liver and not expressed in normal adult liver tissue, but its expression is reactivated in hepatocellular carcinoma, and has close association with the development of liver cancer, where the detection rate of GPC3 expression is relatively high during early stage of liver cancer and increases along with the development of liver cancer. Further, GPC3 is also expressed in tumors such as melanoma, ovarian clear cell carcinoma, yolk sac tumor, neuroblastoma and other tumors. Considering its specifically high expression in hepatocellular carcinoma, melanoma and other tumors, GPC3 has emerged as a useful immunohisto-chemical diagnostic test and potential biomarker.

GPC3 is a member of the proteoglycan family that functions as extracellular matrix in cell adhesion in organogenesis or as a receptor of a cell growth factor. The protein core of GPC3comprises two subunits, and N-terminal sub-unit and a C-terminal subunit. A glycosyl phosphatidylinositol (GPI) anchor is added to serine at position 560 located on the carboxyl (C)-terminal side of GPC3. The GPI anchor plays a role in localizing GPC3 on cell surface through covalent binding to cell membrane lipid. Also, serine at position 495 and serine at position 509of GPC3 are modified with a heparan sulfate chain (HS chain) wherein the HS chain is known to regulate a plurality of growth signal transduction pathways such as Wnt signal, FGF signal, and BMP signal transduction pathways. A growth signal trans-duction pathway involved is known to differ among the types of cancers. For example, in hepatocellular carcinoma (HCC), cells grow by the stimulation of the Wnt signal pathway.

GPC3 CAR

The present disclosure provides, at least in part, GPC3 CAR polypeptides. As used herein, "chimeric antigen recep-tor (CAR)" refers to a receptor not present in nature and is capable of providing an immune effector cell with a speci-ficity to a particular antigen. In some embodiments, a CAR refers to a receptor used for delivering the specificity of a monoclonal antibody agent to a T cell. Generally, a CAR comprises an extracellular binding domain (Ectodomain), a transmembrane domain, and an intracellular signaling domain (Endodomain). In some embodiments, an extracel-lular binding domain of a CAR comprises an antigen bind-ing domain. In some embodiments, an antigen binding domain is or comprises an antibody agent. In some embodi-ments, an antigen binding domain is or comprises an anti-body agent that specifically binds to GPC3.

In some embodiments, the chimeric antigen receptor (CAR) polypeptide includes: i) an extracellular antigen-binding domain comprising a light chain variable domain comprising a light chain CDR1 comprising SEQ ID NO: 1; a light chain CDR2 comprising SEQ ID NO: 2;and a light chain CDR3 comprising SEQ ID NO: 3; and a heavy chain variable domain comprising a heavy chain CDR1 compris-ing SEQ ID NO: 4; a heavy chain CDR2 comprising SEQ ID NO: 5; and a heavy chain CDR3 comprising SEQ ID NO: 6; ii) a transmembrane domain; and iii) an intracellular signal-ing domain, which leads to T cell activation when an antigen binds to the antibody agent.

TABLE 1

| SEQ ID NO: | | SEQUENCE |
|---|---|---|
| 1 | Light chain CDR1 | RSSQSLVHSNGNTYLH |
| 2 | Light chain CDR2 | KVSNRFS |
| 3 | Light chain CDR3 | SQNTHVPPT |
| 4 | Heavy chain CDR1 | DYEMH |
| 5 | Heavy chain CDR2 | ALDPKTGDTAYSQKFKG |
| 6 | Heavy chain CDR3 | FYSYTY |

In some embodiments, the CAR polypeptide includes: i) an extracellular antigen-binding domain comprising a light chain variable domain comprising a sequence that is at least 80%, 85%, 90%, 91%, 92%, 93%, 94%, 95%, 96%, 97%, 98%, or 99% identical to SEQ ID NO: 10and a heavy chain variable domain comprising a sequence that is at least 80%, 85%, 90%, 91%, 92%, 93%, 94%, 95%, 96%, 97%, 98%, or 99% identical to SEQ ID NO: 8; ii) a transmembrane domain; and iii) an intracellular signaling domain, which leads to T cell activation when an antigen binds to the antibody agent.

In some embodiments, the CAR polypeptide includes: i) an extracellular antigen-binding domain comprising a light chain variable domain comprising SEQ ID NO: 10 and a heavy chain variable domain comprising SEQ ID NO: 8; ii) a transmembrane domain; and iii) an intracellular signaling domain, which leads to T cell activation when an antigen binds to the antibody agent.

TABLE 2

| SEQ ID NO: | NAME | TYPE | SEQUENCE |
|---|---|---|---|
| 7 | huGC33 VH | Nucleotide | CAAGTGCAACTCGTACAATCAGGTGCTGAAGTCA AAAAGCCGGGAGCCTCTGTTAAAGTGTCCTGTAA AGCCAGCGGCTACACCTTTACCGATTATGAGATG CACTGGGTTCGGCAGGCTCCGGGCCAAGGTCTCG AGTGGATCGGGGCTCTTGACCCAAAGACGGGCG ACACGGCTTATTCACAAAAATTCAAAGGTAGGGC TACTCTGACTGCCGATAAGTCCACCAGCACCGCG TATATGGAGCTCTCTAGCTTGCGAAGCGAGGACA CGGCGGTGTACTATTGCACACGCTTCTATAGTTA CACATATTGGGGTCAAGGCACGCTTGTGACCGTG TCTAGC |
| 8 | | Amino acid | QVQLVQSGAEVKKPGASVKVSCKASGYTFTDYEM HWVRQAPGQGLEWIGALDPKTGDTAYSQKFKGRA TLTADKSTSTAYMELSSLRSEDTAVYYCTRFYSYT YWGQGTLVTVSS |
| 9 | huGC33 VL | Nucleotide | GACGTCGTTATGACACAGAGTCCCCTCTCCTTGC CGGTGACCCTGGGTCAGCCTGCGTCCATCTCTTG CAGATCCTCCCAGTCTCTGGTACACTCCAACGGC AACACATACTTGCACTGGTACCAACAAAGACCTG GTCAGTCACCGCGACTTCTCATATATAAAGTTTC CAATAGGTTCAGTGGAGTGCCAGACAGGTTCAGT GGTTCAGGATCAGGCACTGATTTCACGCTTAAAA TCAGTCGGGTTGAGGCGGAGGACGTAGGAGTTTA CTATTGCAGCCAGAATACGCACGTGCCGCCTACT TTTGGCTCTGGAACCAAGTTGGAAATAAAG |

TABLE 2-continued

| SEQ ID NO: | NAME | TYPE | SEQUENCE |
|---|---|---|---|
| 10 | | Amino acid | DVVMTQSPLSLPVTLGQPASISCRSSQSLVHSNGNT YLHWYQQRPGQSPRLLIYKVSNRFSGVPDRFSGSGS GTDFTLKISRVEAEDVGVYYCSQNTHVPPTFGSGTK LEIK |
| 11 | muGC33 VH | Nucleotide | CAGGTTCAACTGCAGCAGTCTGGGGCTGAGCTGG TGAGGCCTGGGGCTTCAGTGAAGCTGTCCTGCAA GGCTTCGGGCTACACATTTACTGACTATGAAATG CACTGGGTGAAGCAGACACCTGTGCATGGCCTAA AATGGATTGGAGCTCTTGATCCTAAAACTGGTGA TACTGCCTACAGTCAGAAGTTCAAGGGCAAGGCC ACACTGACTGCAGACAAATCCTCCAGCACAGCCT ACATGGAGCTCCGCAGCCTGACATCTGAGGACTC TGCCGTCTATTACTGTACAAGATTCTACTCCTAT ACTTACTGGGGCCAAGGGACTCTGGTCACTGTCT CTGCA |
| 12 | | Amino acid | QVQLQQSGAELVRPGASVKLSCKASGYTFTDYEM HWVKQTPVHGLKWIGALDPKTGDTAYSQKFKGKA TLTADKSSSTAYMELRSLTSEDSAVYYCTRFYSY TYWGQGTLVTVSA |
| 13 | muGC33 VL | Nucleotide | GATGTTGTGATGACCCAAACTCCACTCTCCCTGCC TGTCAGTCTTGGAGATCAAGCCTCCATCTCTTGC AGATCTAGTCAGAGCCTTGTACACAGTAATGGAA ACACCTATTTACATTGGTACCTGCAGAAGCCAGG CCAGTCTCCAAAGCTCCTGATCTACAAAGTTTCC AACCGATTTTCTGGGGTCCCAGACAGGTTCAGTG GCAGTGGATCAGGGACAGATTTCACACTCAAGAT CAGCAGAGTGGAGGCTGAGGATCTGGGAGTTTAT TTCTGCTCTCAAAATACACATGTTCCTCCTACGT TCGGATCGGGGACCAAGCTGGAAATAAAA |
| 14 | | Amino acid | DVVMTQTPLSLPVSLGDQASISCRSSQSLVHSNGNT YLHWYLQKPGQSPKLLIYKVSNRFSGVPDRFSGSGS GTDFTLKISRVEAEDLGVYFCSQNTHVPPTFGSGTK LEIK |

Nucleic Acids

As used herein, "nucleic acid" is used to include any compound and/or substance that comprise a polymer of nucleotides. In some embodiments, a polymer of nucleotides is referred to as polynucleotides. Exemplary nucleic acids or polynucleotides can include, but are not limited to, ribonucleic acids (RNAs) and/or deoxyribonucleic acids (DNAs).

In some embodiments, nucleic acid constructs include regions that encode a GPC3 CAR. In some embodiments, the CAR polypeptide includes: i) an extracellular antigen-binding domain comprising a light chain variable domain encoded by a nucleic acid comprising a sequence that is at least 80%, 85%, 90%, 91%, 92%, 93%, 94%, 95%, 96%, 97%, 98%, or 99% identical to SEQ ID NO: 9 and a heavy chain variable domain encoded by a nucleic acid comprising a sequence that is at least 80%, 85%, 90%, 91%, 92%, 93%, 94%, 95%, 96%, 97%, 98%, or 99% identical to SEQ ID NO: 7; ii) a transmembrane domain; and iii) an intracellular signaling domain, which leads to T cell activation when an antigen binds to the antibody agent.

In some embodiments, the CAR polypeptide includes: i) an extracellular antigen-binding domain comprising a light chain variable domain encoded by a nucleic acid comprising SEQ ID NO: 9 and a heavy chain variable domain encoded by a nucleic acid comprising SEQ ID NO: 7;ii) a transmembrane domain; and iii) an intracellular signaling domain, which leads to T cell activation when an antigen binds to the antibody agent.

In some embodiments, nucleic acid constructs may be inserted into an expression vector or viral vector by methods known to the art, and nucleic acid molecules may be operably linked to an expression control sequence. Non-limiting examples of expression vectors include plasmid vectors, transposon vectors, cosmid vectors, and viral vectors (e.g., any adenoviral vectors (AV), cytomegaloviral (CMV) vectors, simian viral (SV40) vectors, adeno-associated virus (AAV) vectors, lentiviral vectors, and retroviral vectors). In some embodiments, the expression vector is a viral vector. In some embodiments, the viral vector is a lentiviral vector.

A lentiviral vector is derived from a lentivirus. Lentiviral vectors are based on the single- stranded RNA lentiviruses, which are a subclass of retrovirus. They combine the advantages of midrange cloning capacity with stable gene expression, wherein they are able to transduce dividing and non-dividing cells, including neurons. Upon infection, the lentiviral genome integrates transgenes into the host genome and promotes long-term gene expression. Lentiviral vectors, such as HIV-based vectors, are exemplary of retroviral vectors used for gene delivery. Unlike other retroviruses, HIV-based vectors are known to incorporate their passenger genes into non-dividing cells and, therefore, can be of use in treating persistent forms of disease.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art.

In some embodiments, nucleic acid molecules are inserted into a vector that is able to express a GPC3 CAR of the present disclosure when introduced into an appropriate cell. In some embodiments, an appropriate cell is a T cell.

Production of GPC3 CAR-T cells

Provided herein are methods for producing immune cells comprising a GPC3 CAR. In some embodiments, the immune cell where a CAR is introduced therein is a human immune cell. In some embodiments, the immune cell is an autologous human immune cell. In some embodiments, the immune cell is an allogeneic human immune cell. In some embodiments, the immune cell is a CD4+T cell (helper T cell, TH cell), a CD8+T cell (cytotoxic T cell, CTL), a memory T cell, a regulatory T cell (Treg cell), an apoptotic T cell, but is not limited thereto. In some embodiments, the immune cell is an NK cell.

In some embodiments, the present disclosure provides methods of producing an engineered immune cell, comprising: introducing into an immune cell (i) a nucleic acid encoding a GPC3 CAR, comprising a GPC3 antigen binding domain, or (ii) a vector comprising the nucleic acid encoding a GPC3 CAR, comprising a GPC3 antigen binding domain. In some embodiments, a method of producing an engineered immune cell of the present disclosure further comprises culturing the engineered immune cell in vitro for at least 5 days, 7 days, 9 days, 10days, 11 days, or 12 days.

In some embodiments, the present disclosure provides methods of preparing an autologous engineered immune cell of the present disclosure, comprising: providing or obtaining an analysis of binding of a GPC3 antigen binding domain to an immune cell from a subject; and if the binding is less than a threshold value, engineering an immune cell from the subject to express a CAR comprising the GPC3 antigen binding domain. In some embodiments, a method of producing an autologous engineered immune cell of the present disclosure further comprises culturing the autologous engineered immune cell in vitro for at least 5 days, 7 days, 9 days, 10days, 11 days, or 12 days.

Any method known in the art for expressing a CAR in immune cells can be used in the context of the present disclosure. For example, there are various nucleic acid vectors for expression known in the art, such as linear polynucleotides, polynucleotides to which an ionic or amphiphilic compound is bound, plasmids, or viral vectors, though the present disclosure is not limited thereto. In some embodiments, a vector for expression of a CAR in immune cells may be or include an autonomously replicating plasmid or virus or derivative thereof. Viral vectors can include, but are not limited to adenovirus vector, adeno-associated viral vector, retrovirus vector, etc. In some embodiments a lentivirus vector, which is a retroviral vector, can be used. In some embodiments, a vector is a non-plasmid and a non-viral compound, such as, for example, a liposome.

The present disclosure encompasses the recognition that GPC3 CAR-T cells, generated by the methods described herein may be therapeutically useful (e.g., for the treatment of cancer).

Therapeutic Applications

Provided herein are methods of treating a subject having a glypican-3-associated cancer, wherein the method comprises administering to a subject a composition that comprises or delivers an immune cell comprising a GPC3 CAR.

A "glypican-3-associated cancer" is a cancer that is characterized by a cancer cell having glypican-3 present on its surface. GPC3, a membrane-bound heparan sulfate proteoglycan, is overexpressed in approximately 70% to 80% of hepatocellular carcinomas, but is not expressed commonly in healthy tissues. In addition, GPC3 overexpression is found in several tumors, most notably in hepatocellular carcinomas, hepatoblastoma, germ cell tumors (e.g., yolk sac tumors, choriocarcionomas), Wilms tumor, gastric carcinoma, non-small lung cancer, and thyroid cancer.

Cancer can refer to a broad group of diseases characterized by the uncontrolled growth of abnormal cells in the body. Unregulated cell division and growth results in the formation of malignant tumors that invade neighboring tissues and may also metastasize to distant parts of the body through the lymphatic system or bloodstream. Cancer or cancer tissue may include a tumor.

Cancers suitable for treatment by a method of the present disclosure can include, but are not limited to, bladder cancer, breast cancer, cervical cancer, colon cancer, endometrial cancer, esophageal cancer, fallopian tube cancer, gall bladder cancer, gastrointestinal cancer, head and neck cancer, hematological cancer, laryngeal cancer, liver cancer, lung cancer, lymphoma, melanoma, mesothelioma, ovarian cancer, primary peritoneal cancer, salivary gland cancer, sarcoma, stomach cancer, thyroid cancer, pancreatic cancer, and prostate cancer. In some embodiments, a cancer for treatment by a method of the present disclosure can include may include, but is not limited to, carcinoma, lymphoma (e.g., Hodgkin's and non-Hodgkin's lymphomas), blastoma, sarcoma, and leukemia. In some embodiments, cancer may include squamous cell carcinoma, small cell lung cancer, non-small cell lung cancer, lung adenocarcinoma, squamous cell carcinoma of the lung, peritoneal cancer, hepatocellular carcinoma, gastric cancer, pancreatic cancer, glioma, cervical cancer, ovarian cancer, liver cancer, bladder cancer, hepatocellular carcinoma, breast cancer, colon cancer, colorectal cancer, endometrial or uterine carcinoma, salivary carcinoma, kidney cancer, prostate cancer, vulvar cancer, thyroid cancer, liver carcinoma, leukemia and other lymphoproliferative disorders, and various types of head and neck cancer.

In some embodiments, the cancer can be an embryonal tumor (Wilms tumor, hepatoblastoma, rhabdoid, neuroblastoma), germ cell tumor (yolk sac tumor, immature teratoma, and embryonal carcinoma), carcinoma (hepatocellular carcinoma and pulmonary squamous cell carcinoma), sarcoma (malignant rhabdoid tumor and RMS), or malignant melanoma. In some embodiments, a glypican-3-associated cancer is a liver cancer.

The immune cells (e.g., CAR-T cells) may be administered at a therapeutically effective amount to a patient in need thereof. For example, a therapeutically effective amount of the immune cells (e.g. CAR-T cells) may be at least about $10^4$ cells, at least about $10^5$ cells, at least about $10^6$ cells, at least about $10^7$ cells, at least about $10^8$ cells, at least about $10^9$, or at least about $10^{10}$. In some embodiments, a therapeutically effective amount of T cells is about $10^4$ cells, about $10^5$ cells, about $10^6$ cells, about $10^7$ cells, about $10^8$ cells, about $10^9$ cells, or about $10^{10}$cells. In some embodiments, the therapeutically effective amount of the T cells is between about $0.1\times10^6$ and about $2\times10^{10}$ T cells (e.g., about $0.1\times10^6$ and about $2\times10^{10}$ T cells, about $0.2\times10^6$and about $2\times10^{10}$ T cells, about $0.4\times10^6$ and about $2\times10^{10}$ T cells, about $0.6\times10^6$ and about $2\times10^{10}$ T cells, about $0.8\times10^6$ and about $2\times10^{10}$ T cells, about $1.0\times10^6$ and about $2\times10^{10}$ T cells, about $2.0\times10^6$ and about $2\times10^{10}$ T cells, about $3.0\times10^6$ and about $2\times10^{10}$ T cells, about $4.0\times10^6$and about $2\times10^{10}$ T cells, about $5.0\times10^6$ and about $2\times10^{10}$ T cells, about $6.0\times10^6$ and about $2\times10^{10}$ T cells, about $7.0\times10^6$ and about $2\times10^{10}$ T cells, about $8.0\times10^6$ and about $2\times10^{10}$ T cells, about $9.0\times10^6$ and about $2\times10^{10}$ T cells, about $1.0\text{x}10^7$ and about $2\times10^{10}$ T cells, about $2.0\text{x}10^7$and about $2\times10^{10}$ T cells, about $3.0\times10^7$ and about $2\times10^{10}$ T cells, about $4.0\times10^7$ and about $2\times10^{10}$ T cells, about $5.0\times10^7$ and about $2\times10^{10}$ T cells, about $6.0\times10^7$ and about $2\times10^{10}$ T cells, about $7.0\times10^7$ and about $2\times10^{10}$ T cells, about $8.0\times10^7$ and about $2\times10^{10}$ T cells, about $9.0\times10^7$and about $2\times10^{10}$ T cells, about $1.0\times10^8$ and about $2\times10^{10}$ T cells, about $2.0\times10^8$ and about $2\times10^{10}$ T cells, about $3.0\times10^8$ and about $2\times10^{10}$ T cells, about $4.0\times10^8$ and about $2\times10^{10}$ T cells, about $5.0\times10^8$ and about $2\times10^{10}$ T cells, about $6.0\times10^8$ and about $2\times10^{10}$ T cells, about $7.0\times10^8$and about $2\times10^{10}$ T cells, about $8.0\times10^8$ and about $2\times10^{10}$ T cells, about $9.0\times10^8$ and about $2\times10^{10}$ T cells, about $1.0\times10^9$ and about $2\times10^{10}$ T cells, about $2.0\times10^9$ and about $2\times10^{10}$ T cells, about $3.0\times10^9$ and about $2\times10^{10}$ T cells, about $4.0\times10^9$ and about $2\times10^{10}$ T cells, about $5.0\times10^9$and about $2\times10^{10}$ T cells, about $6.0\times10^9$ and about $2\times10^{10}$ T cells, about $7.0\times10^9$ and about $2\times10^{10}$ T cells, about $8.0\times10^9$ and about $2\times10^{10}$ T cells, about $9.0\times10^9$ and about $2\times10^{10}$ T cells, or about $1.0\times10^{10}$ and about $2\times10^{10}$ T cells. In some embodiments, the therapeutically effective amount of the T cells is about $0.4\times10^{8,}$ about $0.5\times10^8$, about $0.6\times10^8$, about $0.7\times10^8$, about $0.8\times10^8$, about $0.9\times10^{8,}$ about $1.0\times10^8$, about $1.1\times10^8$, about $1.2\times10^8$, about $1.3\times10^8$, about $1.4\times10^8$, about $1.5\times10^{8,}$ about $1.6\times10^8$, about $1.7\times10^{8,}$ about $1.8\times10^8$, about $1.9\times10^8$, or about $2.0\times10^8$ T cells.

In some embodiments, a therapeutically effective amount of the CAR T cells is about $2\times10^6$ cells/kg, about $3\times10^6$ cells/kg, about $4\times10^6$ cells/kg, about $5\times106$ cells/kg, about $6\times10^6$ cells/kg, about $7\times10^6$ cells/kg, about $8\times10^6$ cells/kg, about $9\times106$ cells/kg, about $1\times10^7$ cells/kg, about $2\times10^7$ cells/kg, about $3\times10^7$ cells/kg, about $4\times107$ cells/kg, about $5\times10^7$ cells/kg, about $6\times10^7$ cells/kg, about $7\times10^7$ cells/kg, about $8\times107$ cells/kg, or about $9\times10^7$ cells/kg. In some embodiments, a therapeutically effective amount of immune cells (e.g., CAR-T cells) is between about $1\times10^6$ and about $2\times10^6$ T cells per kg body weight up to a maximum dose of about $1\times10^{10}$ T cells. In some embodiments, the therapeutically effective amount of the T cells is about $1\times10^6$ or about $2\times10^6$ T cells per kg body weight up to a maximum dose of about $1\times10^{10}$ T cells.

The number of cells will depend upon the ultimate use for which the composition is intended as will the type of cells included therein. For example, in some embodiments, a population of T cells comprising a GPC3 CAR will contain greater than 10%, greater than 15%, greater than 20%, greater than 25%, greater than 30%, greater than 35%, greater than 40%, greater than 45%, greater than 50%, greater than 55%, greater than 60%, greater than 65%, greater than 70%, greater than 75%, greater than 80%, greater than 85%, or greater than 90% of such cells. In some embodiments, a population of T cells comprising a GPC3 CAR will contain about 10% to about 90%, about 10% to about 80%, about 10% to about 70%, about 10% to 60%, about 10% to about 50%, about 10% to about 40%, about 10% to about 30%, about 10% to about 20%, about 10% to about 15%, about 15% to about 90%, about 15% to about 80%, about 15% to about 70%, about 15% to about 60%, about 15% to about 50%, about 15% to about 40%, about 15% to about 30%, about 15% to about 20%, about 20% to about 90%, about 20% to about 80%, about 20% to about 70%, about 20% to about 60%, about 20% to about 50%, about 20% to about 40%, about 20% to about 30%, about 30% to about 90%, about 30% to about 80%, about 30% to about 70%, about 30% to about 60%, about 30% to about 50%, about 30% to about 40%, about 40% to about 90%, about 40% to about 80%, about 40% to about 70%, about 40% to about 60%, about 40% to about 50%, about 50% to about 90%, about 50% to about 80%, about 50% to about 70%, about 50% to about 60%, about 60% to about 90%, about 60% to about 80%, about 60% to about 70%, about 70% to about 90%, about 70% to about 80%, or about 80% to about 90% of such T cells. In some embodiments, a population of T cells for administration is in a volume of a liter or less. In some embodiments, T cells for administration are in a volume of less than 500ml, less than 250 ml, or 100 ml or less. In some embodiments, a density of the desired T cells is typically greater than 106 cells/ml and generally is greater than 107 cells/ml, generally 108cells/ml or greater. A clinically relevant number of immune cells can be apportioned into multiple infusions that cumulatively equal or exceed 107 cells, 108 cells, 109 cells, 1010 cells, 1011cells, or 1012 cells.

In some embodiments, a composition may be administered to a patient parenterally. In some embodiments, a composition that comprises or delivers a T cell comprising a GPC3 CAR may be parenterally administered to a patient in one or multiple administrations. In some embodiments, a composition that comprises or delivers a T cell comprising a GPC3 CAR may be parenterally administered to a patient once every day, once every 2 to 7 days, once every week, once every two weeks, once every month, once every three months, or once every 6 months.

In some embodiments, the present disclosure provides methods of inducing an immune response in a subject in need thereof, the method comprising administering to the subject a composition that comprises or delivers a T cell comprising a GPC3 CAR. In some embodiments a T cell comprising a GPC3 CAR is an autologous T cell. In some embodiments, the present disclosure provides methods of inducing an immune response in a subject in need thereof, the method comprising administering to the subject a composition that comprises or delivers a T cell comprising a nucleic acid and/or vector encoding a GPC3 CAR. In some embodiments a T cell comprising a nucleic acid and/or vector encoding a GPC3 CAR is an autologous T cell. In some embodiments, a subject has or is at risk for developing cancer.

In some embodiments, the present disclosure provides methods of enhancing an immune response in a subject in need thereof, the method comprising administering to the subject a composition that comprises or delivers a T cell comprising a GPC3 CAR. In some embodiments, a T cell comprising a GPC3 CAR is an autologous T cell. In some embodiments, the present disclosure provides methods of enhancing an immune response in a subject in need thereof, the method comprising administering to the subject a composition that comprises or delivers a T cell comprising a nucleic acid and/or vector encoding a GPC3 CAR. In some embodiments a T cell comprising a nucleic acid and/or vector encoding a GPC3 CAR is an autologous T cell. In some embodiments, a subject has or is at risk for developing cancer.

In some embodiments, a disease suitable for treatment with compositions and methods of the present disclosure is selected from a proliferative disease such as a cancer or malignancy or a precancerous condition. In some embodiments, a disease is associated with expression of GPC3.In some embodiments, a disease suitable for treatment with compositions and methods of the present disclosure is a cancer. In some embodiments, a cancer expresses a GPC3 antigen. In some embodiments, a cancer cell has increased expression of GPC3 antigen relative to a non-cancer cell from a subject. In some embodiments, GPC3 expression levels can increase in a subject with cancer. In some embodiments, GPC3 expression levels can be undetectable in a healthy subject.

Pharmaceutical Compositions

In some embodiments, the present disclosure provides pharmaceutical compositions that include a T cell comprising a GPC3 CAR and a pharmaceutically acceptable carrier. In some embodiments, a T cell comprising a GPC3 CAR is an autologous T cell. In some embodiments, the present disclosure provides pharmaceutical compositions that include a T cell comprising a nucleic acid and/or vector encoding a GPC3 CAR and a pharmaceutically acceptable carrier. In some embodiments a T cell comprising a nucleic acid and/or vector encoding a GPC3 CAR is an autologous T cell. Compositions of the present disclosure include pharmaceutical compositions that include a T cell comprising a GPC3 CAR and/or a nucleic acid encoding a GPC3 CAR obtained by a method disclosed herein. In some embodiments, a pharmaceutical composition can include a buffer, a diluent, solubilizer, emulsifier, preservative, adjuvant, an excipient, or any combination thereof. In some embodiments, a composition, if desired, can also contain one or more additional therapeutically active substances.

In some embodiments, T cells of the present disclosure are formulated by first harvesting them from their culture medium, and then washing and concentrating the cells in a medium and container system suitable for administration (a "pharmaceutically acceptable" carrier) in a treatment-effective amount. Suitable infusion medium can be any isotonic medium formulation, typically normal saline, Normosol R (Abbott) or Plasma-Lyte A (Baxter), but also 5% dextrose in water or Ringer's lactate can be utilized. The infusion medium can be supplemented with human serum albumin.

In some embodiments, compositions are formulated for parenteral administration. For example, a pharmaceutical composition provided herein may be provided in a sterile injectable form (e.g., a form that is suitable for subcutaneous injection, hepatic artery infusion, or intravenous infusion). For example, in some embodiments, a pharmaceutical composition is provided in a liquid dosage form that is suitable for injection. In some embodiments, a pharmaceutical composition is provided as powders (e.g., lyophilized and/or sterilized), optionally under vacuum, which can be reconstituted with an aqueous diluent (e.g., water, buffer, salt solution, etc.) prior to injection. In some embodiments, a pharmaceutical composition is diluted and/or reconstituted in water, sodium chloride solution, sodium acetate solution, benzyl alcohol solution, phosphate buffered saline, etc. In some embodiments, a powder should be mixed gently with the aqueous diluent (e.g., not shaken).

In some embodiments, a T cell comprising a GPC3 CAR and/or a nucleic acid encoding a GPC3 CAR of the present disclosure is formulated with a pharmaceutically acceptable parenteral vehicle. Examples of such vehicles are water, saline, Ringer's solution, dextrose solution, and 1-10% human serum albumin. Liposomes and nonaqueous vehicles such as fixed oils can also be used. A vehicle or lyophilized powder can contain additives that maintain isotonicity (e.g., sodium chloride, mannitol) and chemical stability (e.g., buffers and preservatives). In some embodiments, a formulation is sterilized by known or suitable techniques. A pharmaceutical composition may additionally comprise a pharmaceutically acceptable excipient, which, as used herein, includes any and all solvents, dispersion media, diluents, or other liquid vehicles, dispersion or suspension aids, surface active agents, isotonic agents, thickening, or emulsifying agents, preservatives, solid binders, lubricants and the like, as suited to the particular dosage form desired. Remington's The Science and Practice of Pharmacy, 21st Edition, A. R. Gennaro (Lippincott, Williams & Wilkins, Baltimore, MD, 2006) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this disclosure.

In some embodiments, a composition including a population of T cells comprising a GPC3 CAR and/or a nucleic acid encoding a GPC3 CAR of the present disclosure is stably formulated. In some embodiments, a stable formulation of a population of T cells comprising a GPC3 CAR and/or a nucleic acid encoding a GPC3 CAR of the present disclosure may comprise a phosphate buffer with saline or a chosen salt, as well as preserved solutions and formulations containing a preservative as well as multi-use preserved formulations suitable for pharmaceutical or veterinary use. Preserved formulations contain at least one known preservative or optionally selected from the group consisting of at least one phenol, m-cresol, pcresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, or mixtures thereof in an aqueous diluent. Any suitable concentration or mixture can be used as known in the art, such as 0.001-5%, or any range or value therein, such as, but not limited to 0.001, 0.003, 0.005, 0.009, 0.01, 0.02, 0.03, 0.05, 0.09, 0.1, 0.2, 0.3, 0.4, 0.5, 0.6, 0.7,0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9,3.0, 3.1, 3.2, 3.3, 3.4, 3.5, 3.6, 3.7, 3.8, 3.9, 4.0, 4.3, 4.5, 4.6, 4.7, 4.8, 4.9, or any range or value therein. Non-limiting examples include, no preservative, 0.1-2% m-cresol (e.g., 0.2, 0.3. 0.4,0.5, 0.9, 1.0%), 0.1-3% benzyl alcohol (e.g., 0.5, 0.9, 1.1, 1.5, 1.9, 2.0, 2.5%), 0.001-0.5% thimerosal (e.g., 0.005, 0.01), 0.001-2.0% phenol (e.g., 0.05, 0.25, 0.28, 0.5, 0.9, 1.0%), 0.0005-1.0% alkylparaben(s) (e.g., 0.00075, 0.0009, 0.001, 0.002, 0.005, 0.0075, 0.009, 0.01, 0.02, 0.05,0.075, 0.09, 0.1, 0.2, 0.3, 0.5, 0.75, 0.9, 1.0%), and the like.

In some embodiments, a pharmaceutical composition is provided in a form that can be refrigerated and/or frozen. In some embodiments, a pharmaceutical composition is provided in a form that cannot be refrigerated and/or frozen. In some embodiments, reconstituted solutions and/or liquid dosage forms may be stored for a certain period of time after reconstitution (e.g., 2hours, 12 hours, 24 hours, 2 days, 5 days, 7 days, 10 days, 2 weeks, a month, two months, or longer). In some embodiments, storage of compositions including an antibody agent for longer than the specified time results in degradation of the antibody agent. Liquid dosage forms and/or reconstituted solutions may comprise particulate matter and/or discoloration prior to administration. In some embodiments, a solution should not be used if discolored or cloudy and/or if particulate matter remains after filtration. General considerations in the formulation and/or manufacture of pharmaceutical agents may be found, for example, in Remington: The Science and Practice of Pharmacy 21st ed., Lippincott Williams & Wilkins, 2005.

In some embodiments, a pharmaceutical composition including a T cell comprising a GPC3 CAR and/or a nucleic acid encoding a GPC3 CAR of the present disclosure can be included in a container for storage or administration, for example, a vial, a syringe (e.g., an IV syringe), or a bag (e.g., an IV bag). A pharmaceutical composition in accordance with the present disclosure may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient that would be administered to a subject and/or a convenient fraction of such a dosage such as, for example, one-half or one-third of such a dosage.

Kits

The present disclosure further provides a kit comprising one or more containers filled with at least one GPC3 CAR and/or a nucleic acid encoding a GPC3 CAR as described herein. Kits may be used in any applicable method, including, for example, therapeutic methods, diagnostic methods, cell proliferation and/or isolation methods, etc. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

In some embodiments, a kit may include one or more reagents for detection (e.g., detection of a GPC3 CAR and/or nucleic acid encoding a GPC3 CAR. In some embodiments, a kit may include a GPC3 CAR and/or a nucleic acid encoding a GPC3 CAR in a detectable form (e.g., covalently associated with detectable moiety or entity). In some embodiments, one or more GPC3 CARs and/or a nucleic acid encoding a GPC3 CAR as provided herein may be included in a kit used for treatment of subjects. In some embodiments, a GPC3 CAR and/or a nucleic acid encoding a GPC3 CAR as provided herein may be included in a kit used for preparing an autologous T cell expressing the GPC3 CAR.

In some embodiments, a kit may provide one, two, three, four or more GPC3 antibody agents, where each is suitable for cloning into a CAR construct. In some embodiments, a kit may provide other reagents for assaying binding affinity of a GPC3 antibody agent and/or GPC3CAR and/or a GPC3 CAR T cell for a T cell or GPC3 identified or isolated from a subject. In some embodiments, a kit may provide other reagents for assaying functional avidity of an antibody agent and/or GPC3 CAR and/or a GPC3 CAR T cell for a T cell of a subject.

EXAMPLES

The disclosure is further described in the following examples, which do not limit the scope of the disclosure described in the claims.

Example 1-Mouse GC33 (muGC33) humanization muGC33 VH humanization

To generate a humanized anti-GC33 antibody (huGC33), a human VH framework comprising a sequence similar to a mouse anti-GPC3 antibody (muGC33) was used to graft the complementarity determining regions (CDR) of the heavy chain variable region (VH) into the human framework. The residues VH48, VH67, VH69, VH71, VH73, VH78, and VH93 were back-mutated to generate the huGC33 VH.

muGC33 VL humanization

To generate a humanized anti-GC33 antibody (huGC33), a human VL framework comprising a sequence similar to a mouse anti-GPC3 antibody (muGC33) was used to graft the complementarity determining regions (CDR) of the light chain variable region (VL) into the human framework. The residues VL36 and VL46 were back-mutated to generate the huGC33VL.

Figure 2:
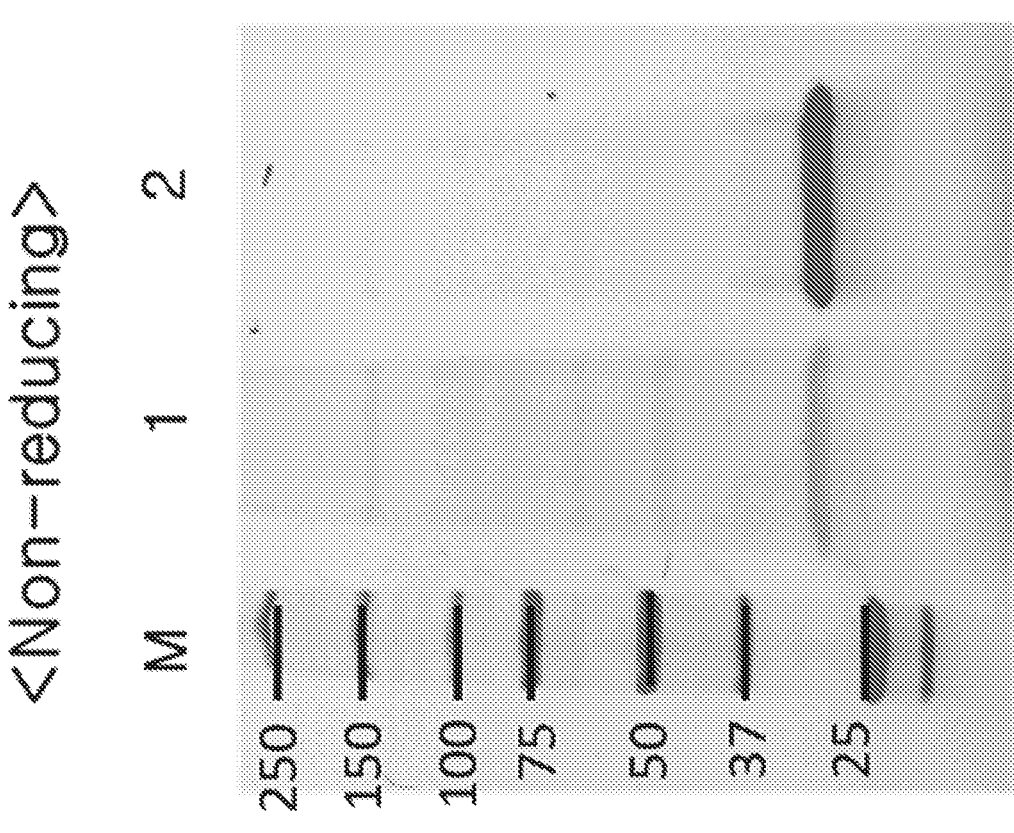
FIG. 2 shows SDS-PAGE results with muGC33 and huGC33 antibodies.

The designed humanized antibody huGC33 was produced in the scFv form. Specifically, the antibodies huGC33 scFv were prepared in the scFv form of VL-(G$_4$S)$_3$-VH in pOptiVEC (Invitrogen) plasmid, which is a mammalian cell expression vector, and a Flag and 6X His tag was conjugated to the c-terminus to prepare the gene (FIG. 1). Plasmids into which the gene was introduced were expressed in scFv form using the Expi293 expression system (Invitrogen), and purified using AktaPure purifier (GE healthcare) and HisTrap column (GE healthcare). The antibodies were added to a blot sample buffer and incubated at 70° C. for 10 minutes to produce a sample for analysis with SDS-PAGE. After running the sample, the final gel was analyzed with Chemidoc (Bio-Rad) (FIG. 2).

Figure 3:
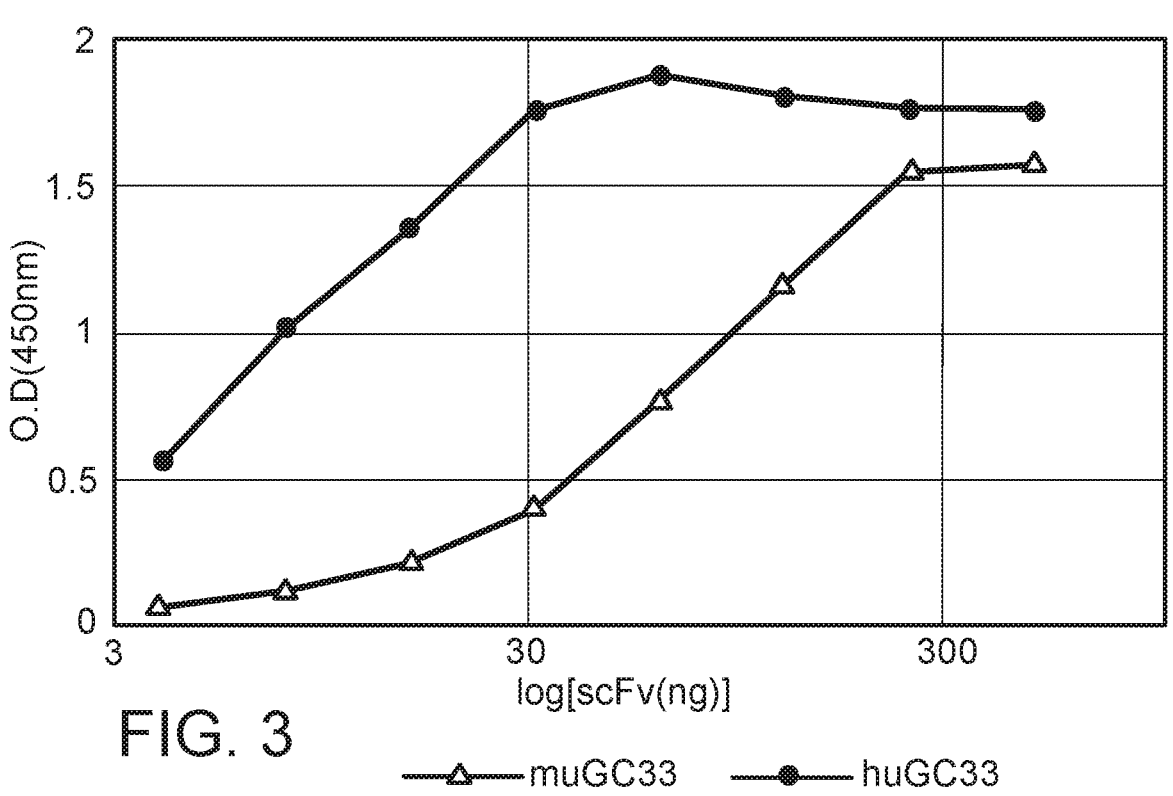
FIG. 3 shows an ELISA titer graph of huGC33 antibodies and muGC33 antibodies.
Figure 4:
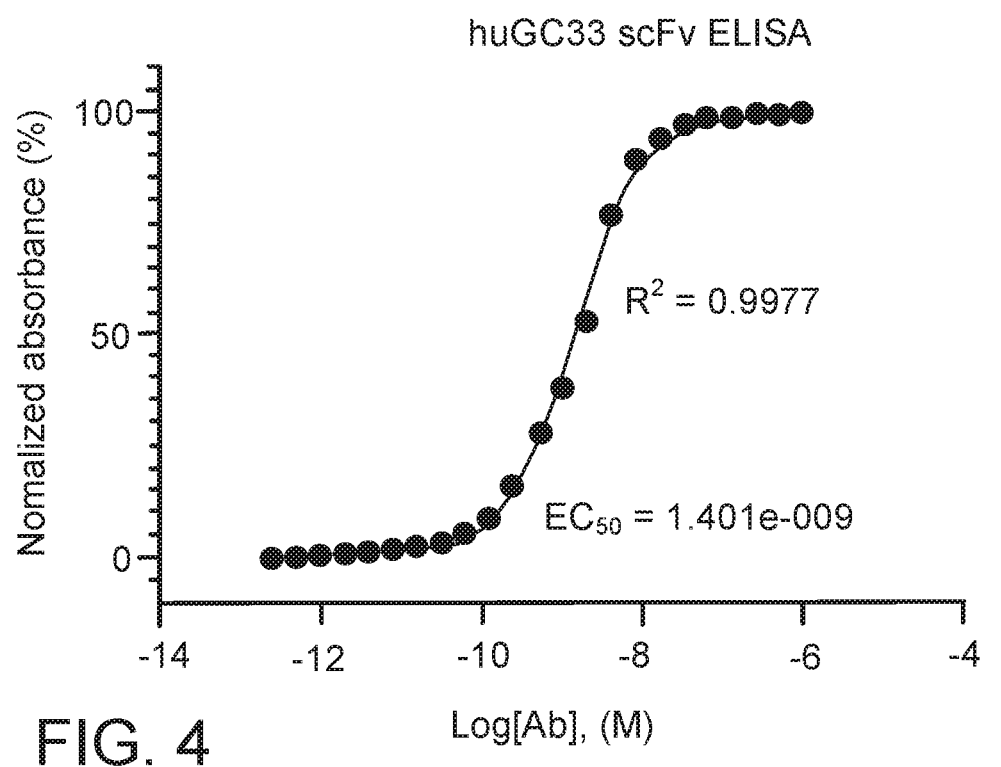
FIG. 4 shows an ELISA titer graph of huGC33 antibodies.

To analyze the binding affinity of muGC33 and huGC33 with antigen Recombinant Human Glypican 3 Protein (GPC3), GPC3 was diluted in 5X ELISA coating buffer, coated in a 96 well immunoplate, and incubated overnight at 4° C. Each well was treated with blocking solution and washed with PBST solution. The antibodies, muGC33 and huGC33, were then added to each well and incubated at room temperature for 1 hour. After the plate was washed, a secondary antibody (Monoclonal ANTI-FLAG M2-Peroxidase (HRP)) was added to each well. The binding affinity was measured and quantified using a microplate reader at 450nm wavelength (FIG. 3). Then, ELISA was repeated to calculate the binding affinity EC50 value of huGC33 scFv. Using the program Prism graphpad, the binding affinity EC50 value was calculated to be 1.401e-009(FIG. 4).

Example 2-Lentiviral transfer plasmid

A DNA construct encoding a single-chain variable fragment (scFv) form (FIG. 1) of a humanized anti-GC33 antibody agent was generated by connecting the VL and VH regions, wherein the sequence is designed to comprise VH-VL orientation or VL-VH orientation, using standard DNA cloning techniques known to the art. The lentiviral transfer plasmids used herein are shown in Table 3 and nucleic acid sequences for both huGC33 VL-VH (SEQ ID NO: 15) and huGC33 VH-VL (SEQ ID NO: 16) are shown in Table 4.

TABLE 3

| Lentiviral Transfer Vector | | |
|---|---|---|
| scFv | Selectable marker | Transfer vector |
| huGC33 VL-VH | Flag | pELPS4 |
| huGC33 VH-VL | Flag | pELPS4 |

TABLE 4

| huGC33 VL-VH (SEQ ID NO: 15) | GACGTCGTTATGACACAGAGTCCCC TCTCCTTGCCGGTGACCCTGGGTCA GCCTGCGTCCATCTCTTGCAGATCC TCCCAGTCTCTGGTACACTCCAACG GCAACACATACTTGCACTGGTACCA ACAAAGACCTGGTCAGTCACCGCGA CTTCTCATATATAAAGTTTCCAATA |
|---|---|

TABLE 4-continued

```
                    GGTTCAGTGGAGTGCCAGACAGGTT
                    CAGTGGTTCAGGATCAGGCACTGAT
                    TTCACGCTTAAAATCAGTCGGGTTG
                    AGGCGGAGGACGTAGGAGTTTACTA
                    TTGCAGCCAGAATACGCACGTGCCG
                    CCTACTTTTGGCTCTGGAACCAAGT
                    TGGAAATAAAGGGTGGCGGCGGAAG
                    TGGTGGTGGTGGTTCTGGGGGCGGG
                    GGTTCCCAAGTGCAACTCGTACAAT
                    CAGGTGCTGAAGTCAAAAAGCCGGG
                    AGCCTCTGTTAAAGTGTCCTGTAAA
                    GCCAGCGGCTACACCTTTACCGATT
                    ATGAGATGCACTGGGTTCGGCAGGC
                    TCCGGGCCAAGGTCTGGAGTGGATC
                    GGGGCTCTTGACCCAAAGACGGGCG
                    ACACGGCTTATTCACAAAAATTCAA
                    AGGTAGGGCTACTCTGACTGCCGAT
                    AAGTCCACCAGCACCGCGTATATGG
                    AGCTCTCTAGCTTGCGAAGCGAGGA
                    CACGGCGGTGTACTATTGCACACGC
                    TTCTATAGTTACACATATTGGGGTC
                    AAGGCACGCTTGTGACCGTGTCTAG
                    C huGC33 VH-VL       CAAGTGCAACTCGTACAATCAGGTG
(SEQ ID NO: 16)    CTGAAGTCAAAAAGCCGGGAGCCTC
                    TGTTAAAGTGTCCTGTAAAGCCAGC
                    GGCTACACCTTTACCGATTATGAGA
                    TGCACTGGGTTCGGCAGGCTCCGGG
                    CCAAGGTCTGGAGTGGATCGGGGCT
                    CTTGACCCAAAGACGGGCGACACGG
                    CTTATTCACAAAAATTCAAAGGTAG
                    GGCTACTCTGACTGCCGATAAGTCC
                    ACCAGCACCGCGTATATGGAGCTCT
                    CTAGCTTGCGAAGCGAGGACACGGC
                    GGTGTACTATTGCACACGCTTCTAT
                    AGTTACACATATTGGGGTCAAGGCA
                    CGCTTGTGACCGTGTCTAGCGGTGG
                    CGGCGGAAGTGGTGGTGGTGGTTCT
                    GGGGGCGGGGGTTCCGACGTCGTTA
                    TGACACAGAGTCCCCTCTCCTTGCC
                    GGTGACCCTGGGTCAGCCTGCGTCC
                    ATCTCTTGCAGATCCTCCCAGTCTC
                    TGGTACACTCCAACGGCAACACATA
                    CTTGCACTGGTACCAACAAAGACCT
                    GGTCAGTCACCGCGACTTCTCATAT
                    ATAAAGTTTCCAATAGGTTCAGTGG
                    AGTGCCAGACAGGTTCAGTGGTTCA
                    GGATCAGGCACTGATTTCACGCTTA
                    AAATCAGTCGGGTTGAGGCGGAGGA
                    CGTAGGAGTTTACTATTGCAGCCAG
                    AATACGCACGTGCCGCCTACTTTTG
                    GCTCTGGAACCAAGTTGGAAATAAA
                    G
```

Figure 5:
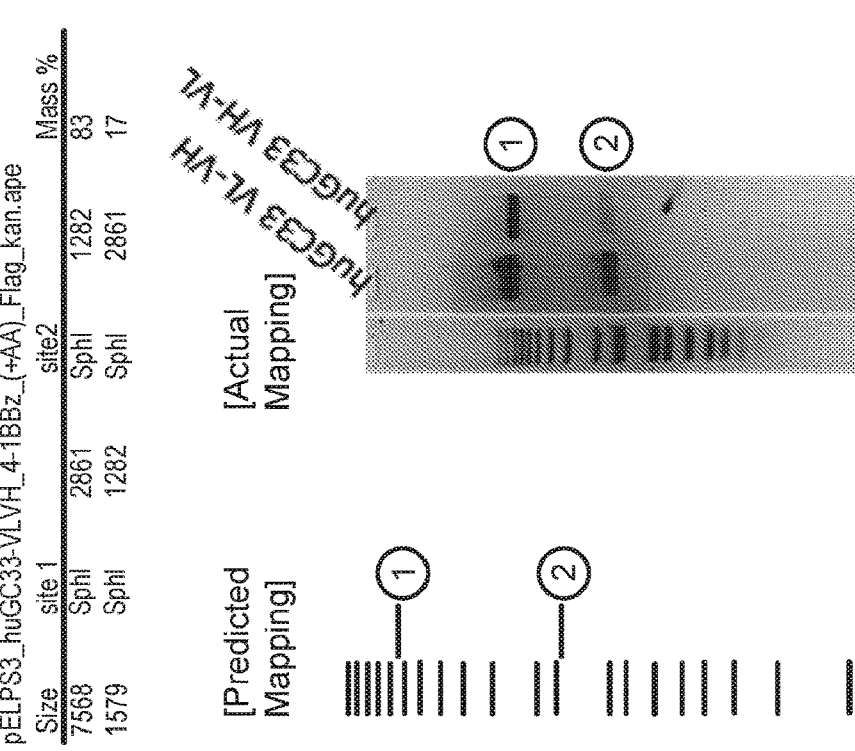
FIG. 5 shows enzyme mapping results for both pELPS4-huGC33 VL-VH and pELPS4-huGC33 VH-VL after cloning.

The lentiviral vector construct, pELPS4-MVRL2H2-eu-BBZ was digested with BamHI and NheI enzymes, and pELPS4 huGC33 VH-VL and pELPS4-huGC33 VL-VH were inserted into the vector construct. DNA fragment purification results are shown in FIG. 5. Transduction units (TU/mL) were also measured for the lentiviruses and shown in Table 5.

TABLE 5

| | | | | Transduction Units (TU/mL) | |
| scFv | Intracellular Domain | Selectable marker | Transfer vector | Production Date | Measurement |
| --- | --- | --- | --- | --- | --- |
| huGC33 VL-VH | euBBz | Flag | pELPS4 | 2019 Sep. 24 | $2.79 \times 10^8$ |
| | | | | 2019 Oct. 21 | $5.95 \times 10^8$ |
| huGC33 VH-VL | euBBz | Flag | pELPS4 | 2019 Sep. 24 | $3.58 \times 10^8$ |
| | | | | 2019 Oct. 21 | $5.22 \times 10^8$ |

Example 3-huGC33-VHVL, huGC33-VLVH CAR-T in vitro

Peripheral blood mononuclear cells (PBMCs) were cultured in a cell culture medium including 1L OpTmizer™M T-Cell Expansion Basal Medium, 25 mL OpTmizer™M T-Cell Expansion Supplement, 50mL CTSTM Immune Cell SR, 10 mL Pen-Strep (10,000 U/mL), and 10mL CTSTM GlutaMAXTM-I Supplement, wherein cell density was adjusted to 1 x 106 cells/mL and IL-2 (400 IU/mL) was added during culture in an incubator at CO2 5% and 37° C.

The immune cells were then transduced with the lentiviral vector and cell growth and expansion was measured from day 5 to day 12 of cell culture. The cells were then harvested on day 12 and used for further analysis.

Figure 6A:
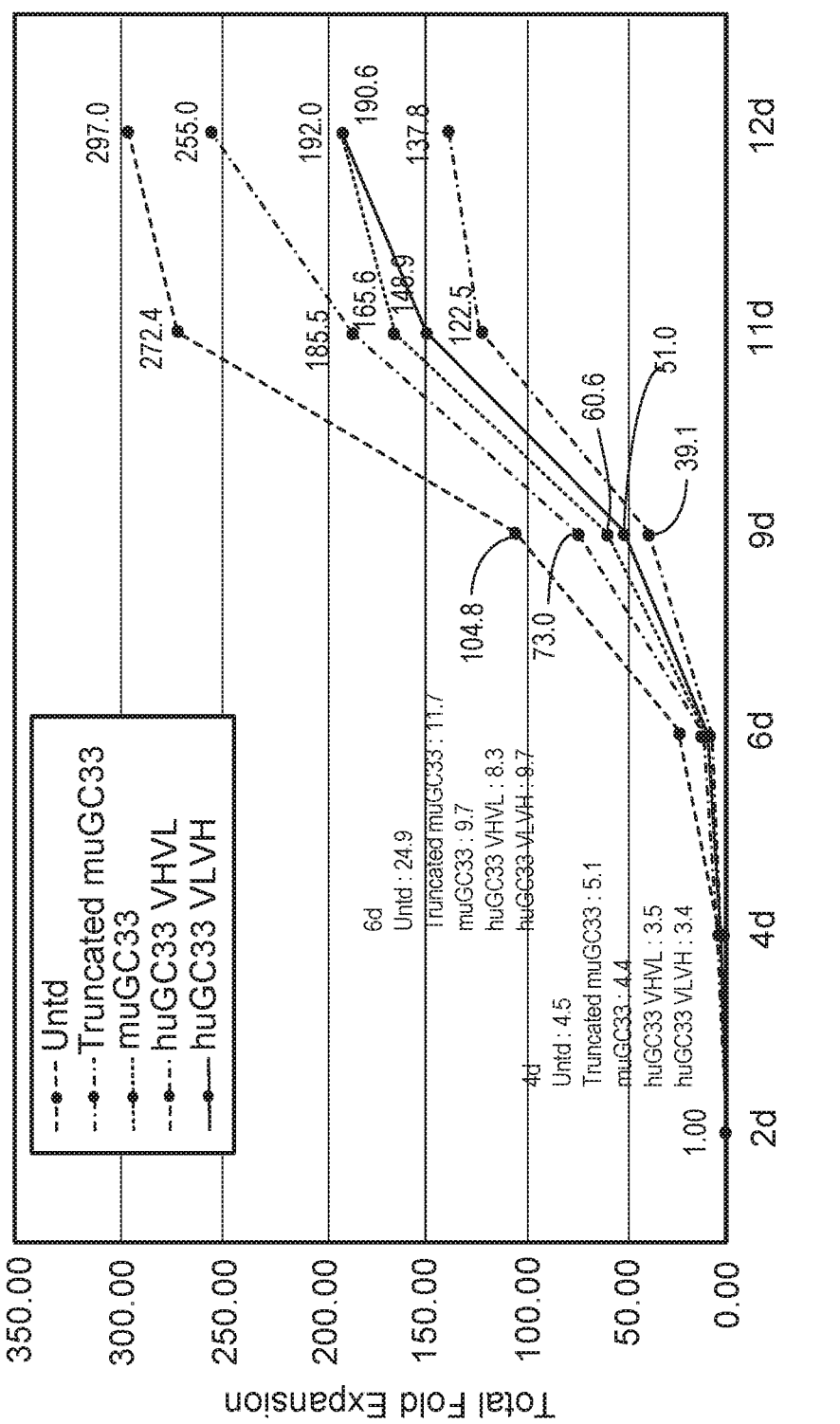
FIG. 6A is a graph showing cell growth for each CAR-T cells, untreated, truncated muGC33,muGC33, huGC33 VHVL, and huGC33 VLVH, on day 12 of cell culture, compared by total fold expansion.
Figure 6B:
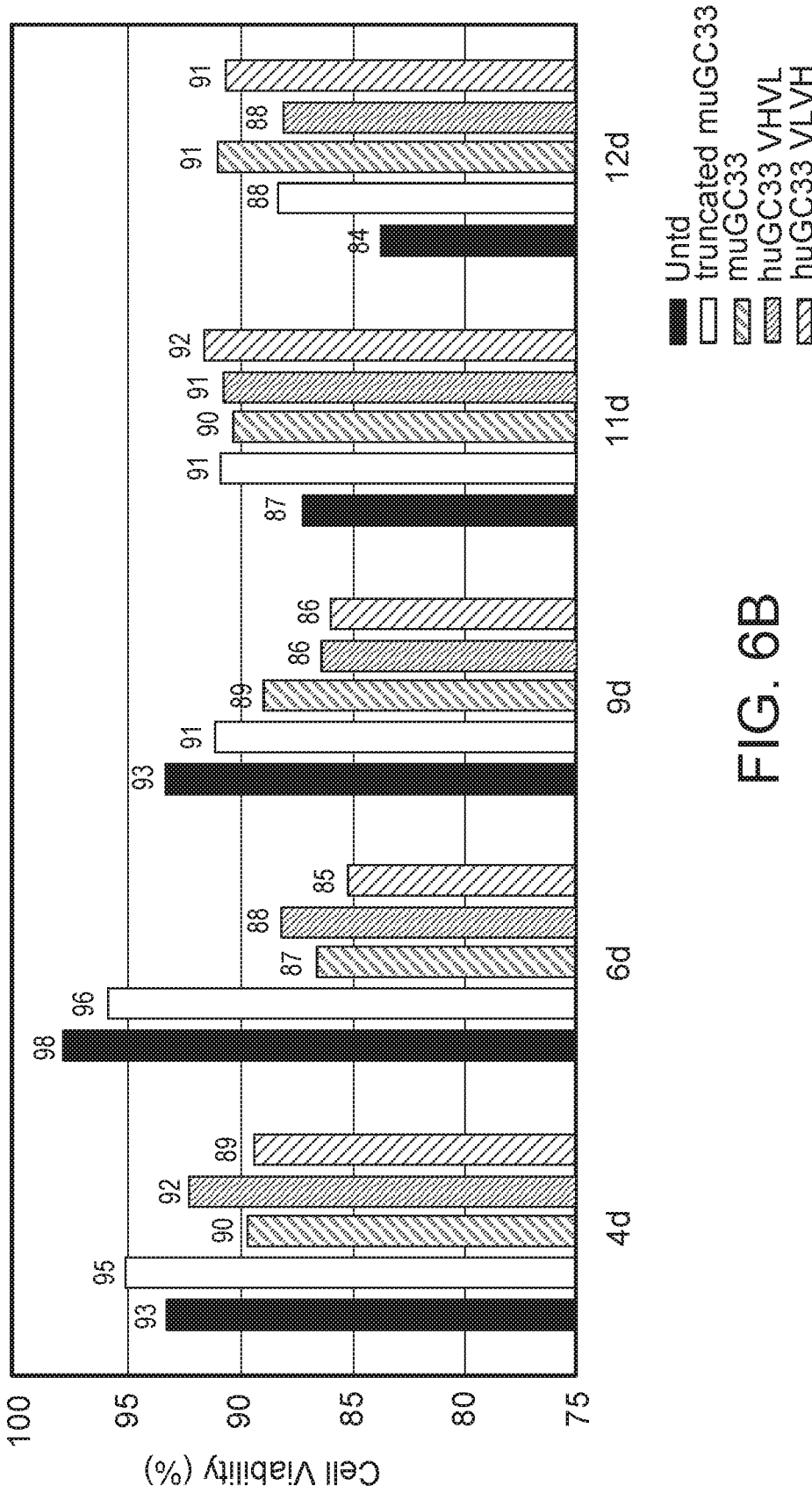
FIG. 6B is a bar graph comparing cell viability of each CAR-T cells, untreated, truncated muGC33, muGC33, huGC33 VHVL, and huGC33 VLVH, from day 4 to day 12.
Figure 7A:
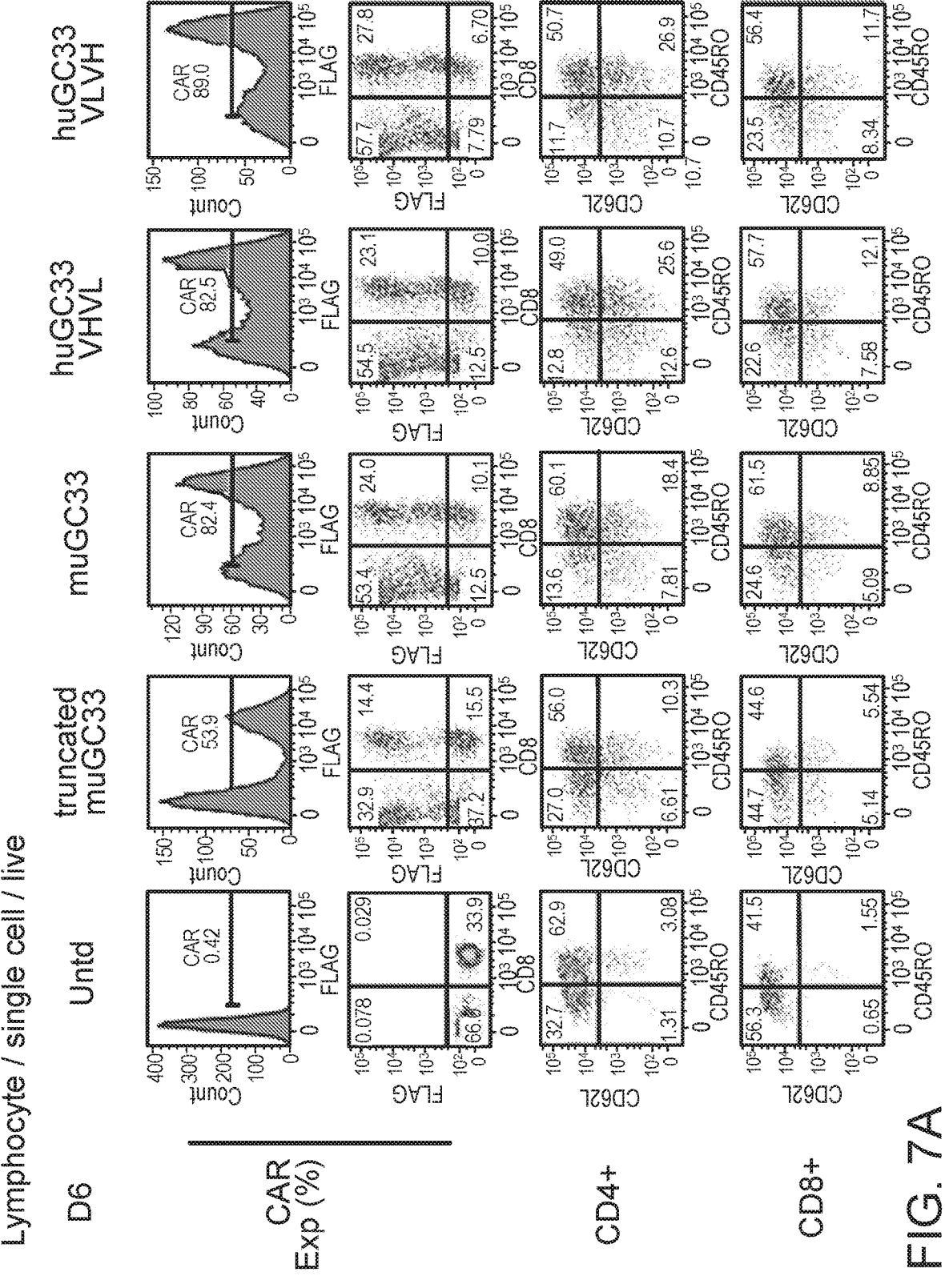
FIG. 7A shows results from FACS analysis of untreated, truncated muGC33, muGC33, huGC33VHVL, and huGC33 VLVH CAR-T cells on day 6.
Figure 7B:
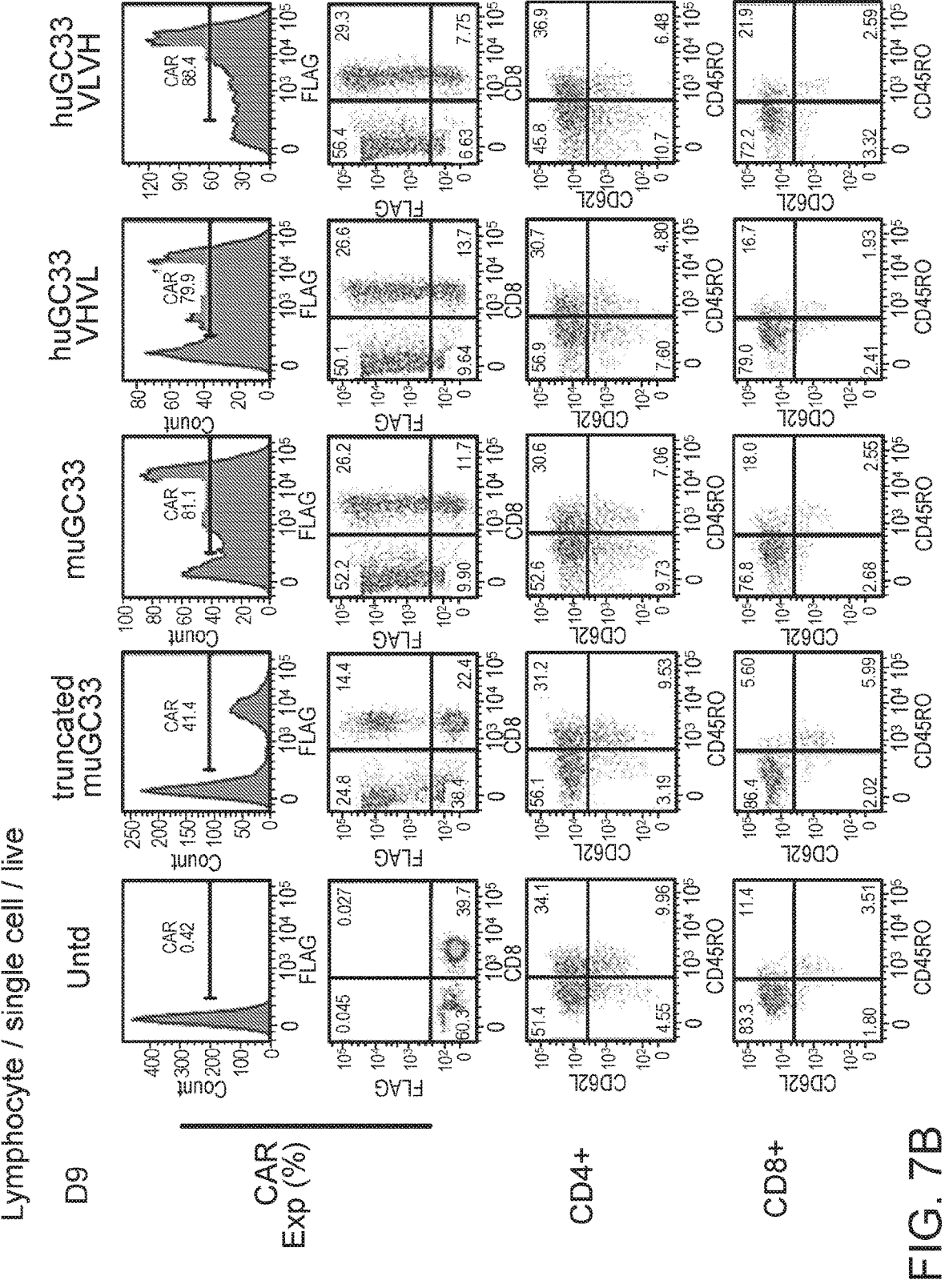
FIG. 7B shows results from FACS analysis of untreated, truncated muGC33, muGC33, huGC33VHVL, and huGC33 VLVH CAR-T cells on day 9.
Figure 7C:
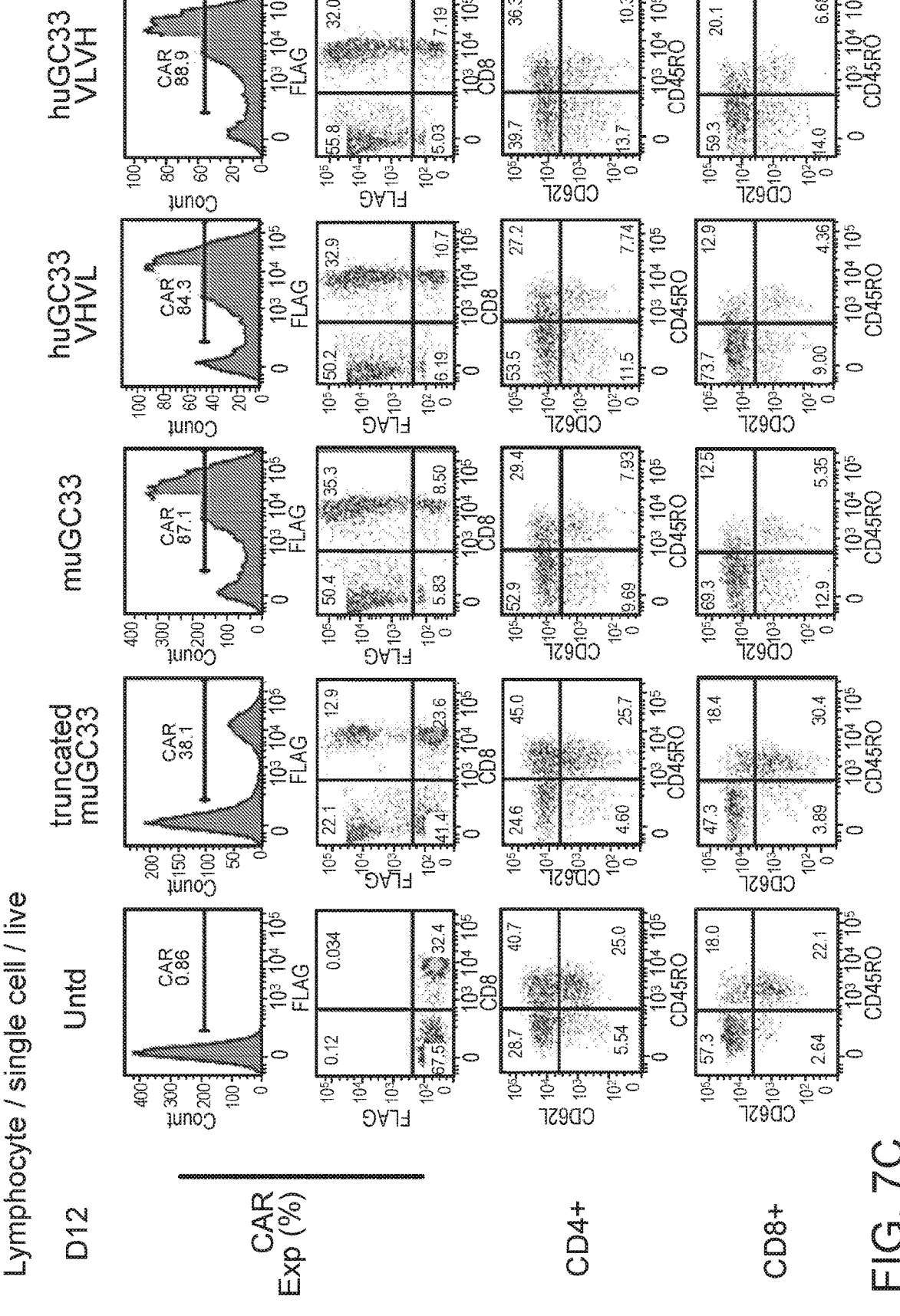
FIG. 7C shows results from FACS analysis of untreated, truncated muGC33, muGC33, huGC33VHVL, and huGC33 VLVH CAR-T cells on day 12.
Figure 8:
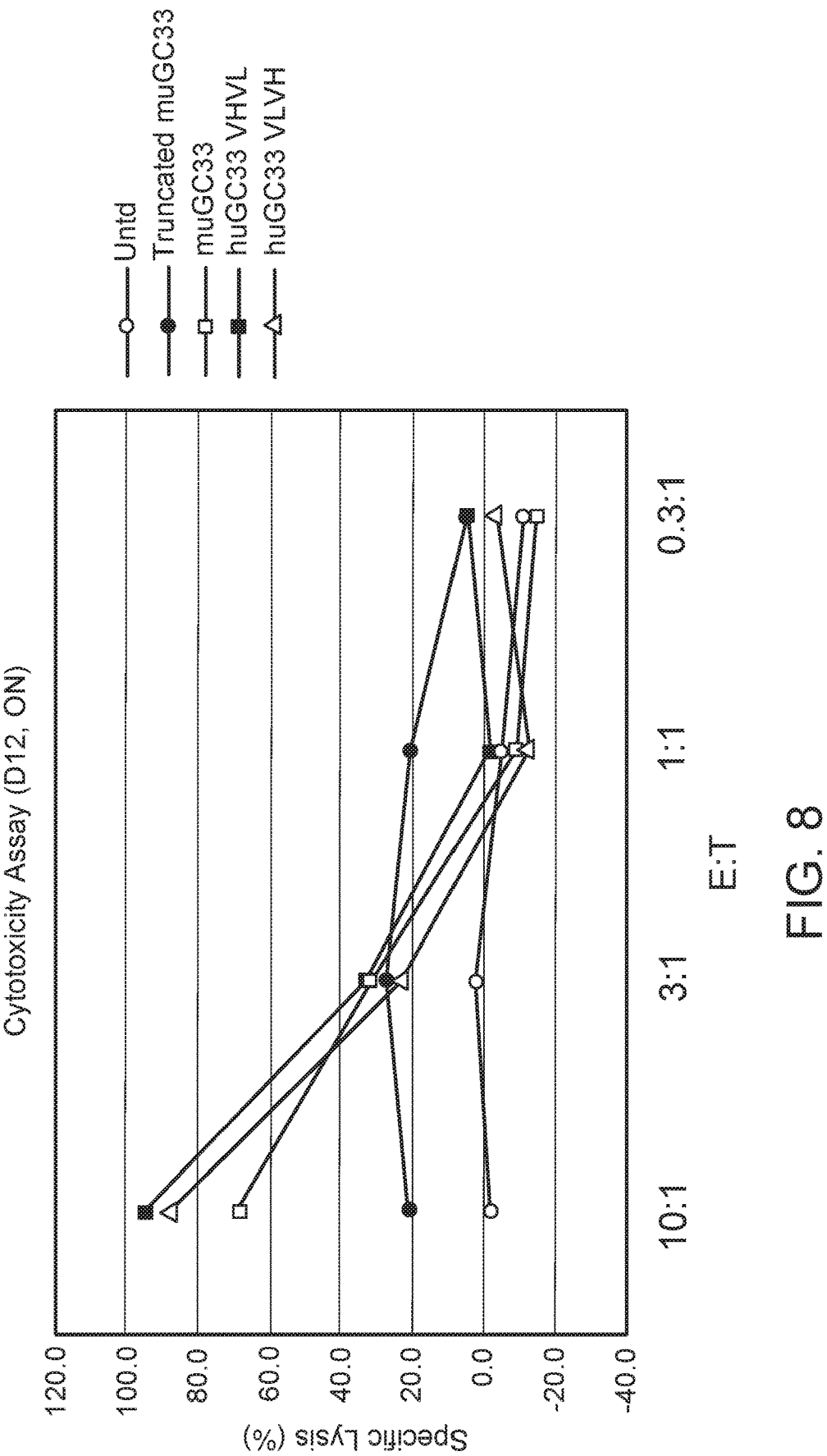
FIG. 8 is a graph comparing results from cytotoxicity assays for untreated, truncated muGC33,muGC33, huGC33 VHVL, and huGC33 VLVH CAR-T cells, wherein the effector (E): target (T) cell ratio (E: T) can be 10:1, 3:1, 1:1, or 0.3:1. Results show that muGC33, huGC33 VHVL, and huGC33 VLVH CAR-T cells showed similar in vitro killing activity, wherein the untreated cells did not show in vitro killing activity.

The huGC33-VHVL and huGC33-VLVH CAR-T constructs were compared in vitro, wherein cell growth for each CAR-T cells on day 12 of cell culture are compared by total fold expansion. Results show that the untreated cells showed a 297.0 fold expansion, truncated muGC33 VHVL cells showed a 255.0 fold expansion, muGC33 VHVL cells showed a 192.0fold expansion, huGC33 VLVH cells showed a 190.6 fold expansion, and huGC33 VHVL cells showed a 137.8 fold expansion (FIG. 6A). Cell expansion and cell viability from day 4 to day 12were compared and while the cell viability of each group of CAR-T cells would differ depending on when the cells were harvested and measured, the results show over 84% viability in all groups of CAR-T cells (FIG. 6B), and CAR expression was analyzed on day 6, day 9, and day 12 of cell culture using flow cytometry (FIGS. 7A-7C). Further, LDH based cytotoxicity assay was performed using Huh-7 cell line (GPC3 positive cell line) to harvest target cells while the CAR-T cells were used as effector cells. The cells were incubated at an E:T ratio of effector (E): target (T)=10:1 in a 96-well U bottom plate, then incubated with Cyto Tox96 reagent for 30 mins, and cytotoxicity was measured and quantified using a microplate reader at 490nm wavelength. (FIG. 8)

Example 4-Expression of GPC3 in liver cancer cells

Figure 9:
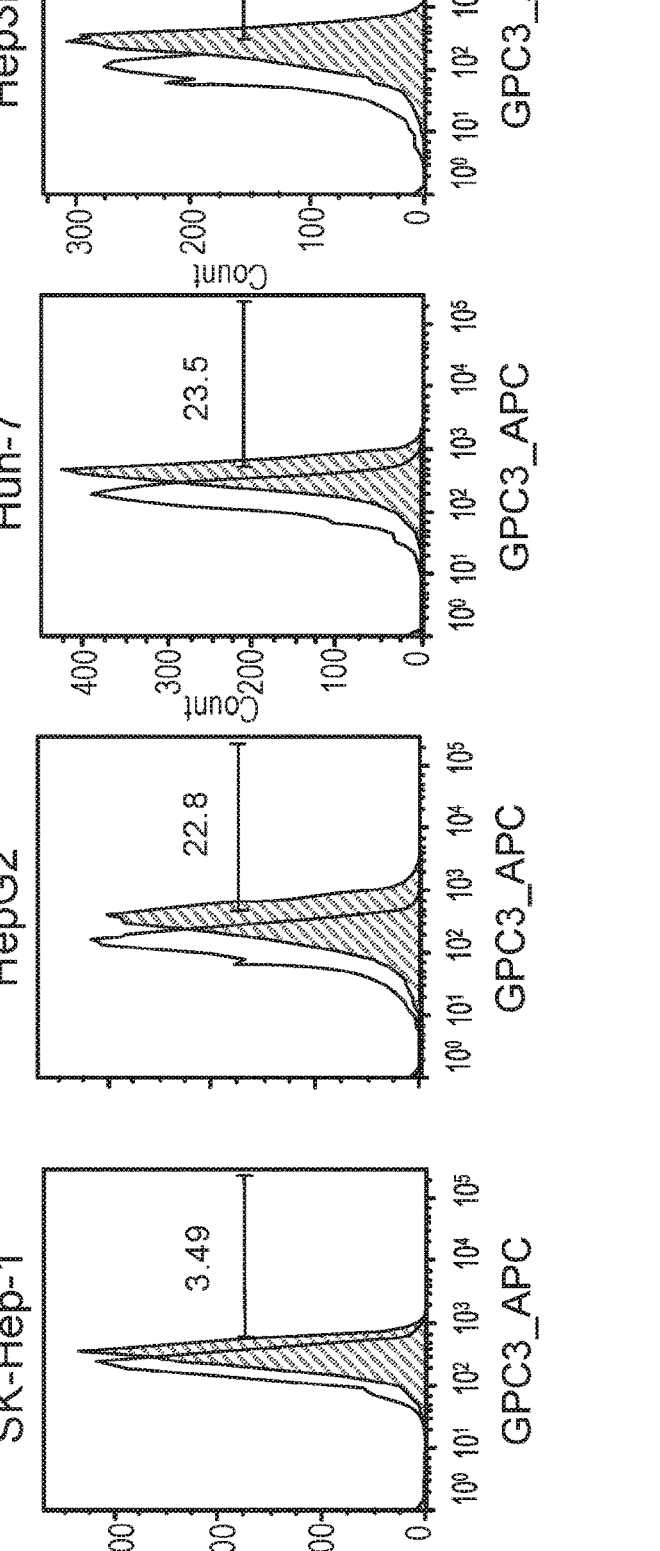
FIG. 9 shows expression of GPC3 in liver cancer cells, wherein GPC3 expression was measured in cell lines HepG2, Hep3B, Huh-7, and SK-Hep-1. Results show that GPC3 was expressed in the HepG2, Hep3B, and Huh-7 cell lines, but not expressed in the SK-Hep-1 cell line.

To develop a liver cancer animal model, a stable cell line expressing luciferase was generated. Three liver cancer cell lines expressing GPC3 and one liver cancer cell which did not express GPC3 were selected. Using the four cell lines, HepG2, Hep3B, Huh-7, and SK-Hep-1,GPC3 expression was determined. Results show that SK-Hep-1 did not show GPC3 expression while HepG2, Hep3B, and Huh-7 showed about 20-30% of GPC3 expression (FIG. 9).

Example 5-Developing a cell line expressing luciferase

Figure 10A:
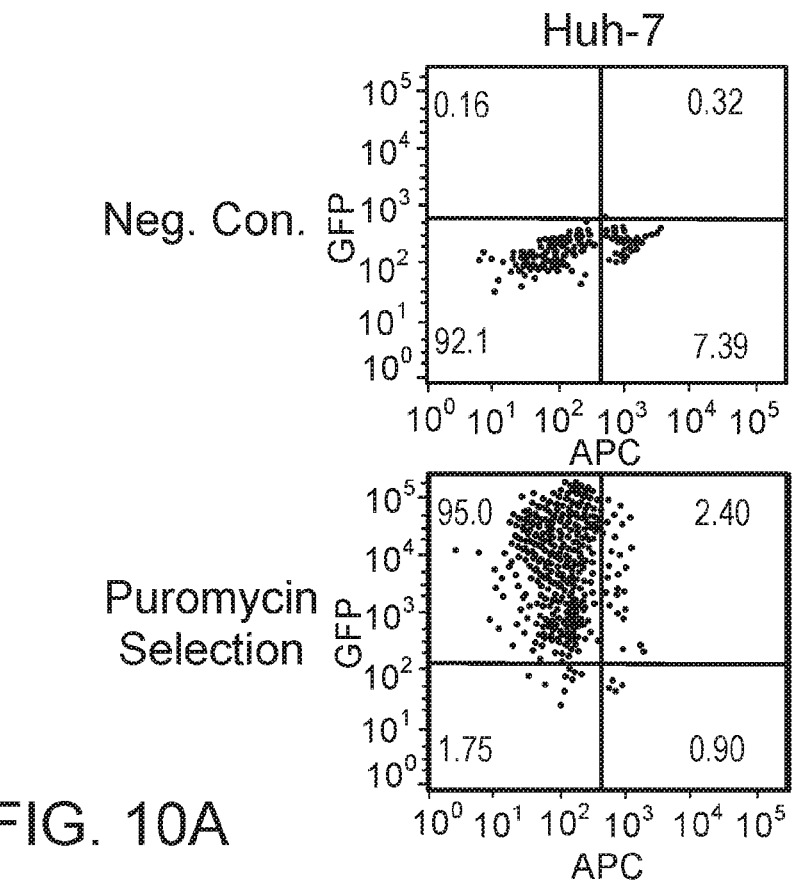
FIG. 10A shows results from FACS analysis from Huh-7 cell line.
Figure 10B:
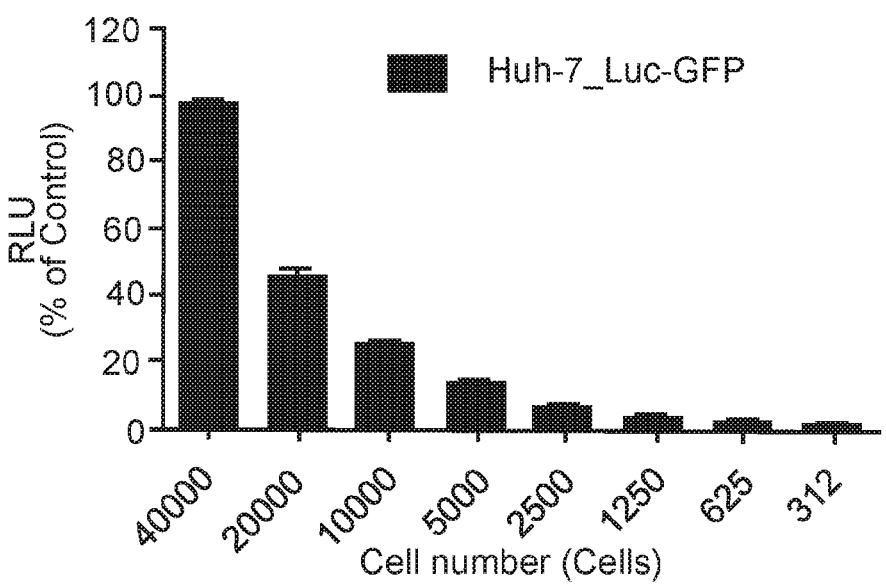
FIG. 10B shows results from Luciferase assays from Huh-7 cell line showing expression of luciferase-GFP.

Using the Huh-7 cell line expressing GPC3 in Example 4, a cell line expressing luciferase-GFP was developed. The cells were transduced with a lentiviral vector and transduction efficiency was determined by GFP expression (FIG. 10A). Then, puromycin was used to selectively isolate the cells transduced with the luciferase-GFP gene and a luciferase function test was administered. Results show that when the number of cells decreased by about 50%, the RLU decreased by about 50% as well (FIG. 10B). These results were used in developing the liver cancer animal model.

Example 6-GPC3 VH-VL CAR-T cells and GPC3 VL-VH CAR-T cells in vivo

Using the three cell lines in Example 4, the cancer cells were injected into NSG mice ($1\times10^6$ cell/head or $2\times1^{06}$ cells/head) and the growth of the liver tumor was observed over a period of time. Results show that the mice injected with Huh-7_Luc-GFP cells showed growth of the tumor over the shortest period of time.

Figure 11:
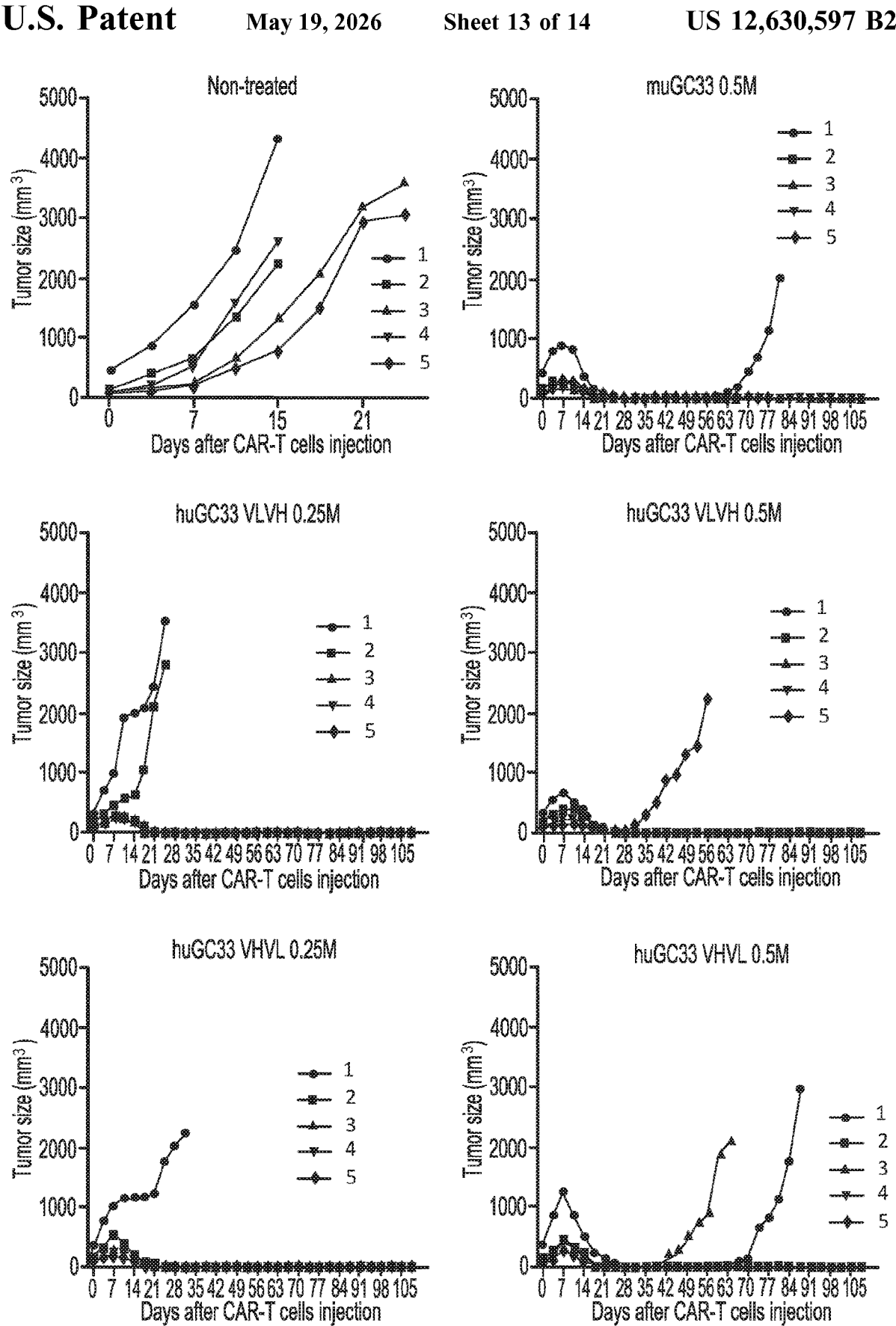
FIG. 11 is a set of graphs showing tumor growth in animal models after GPC3 CAR-T cell injections. Results show 20% of the mice which received huGC33 VHVL showed tumor growth after time of injection, while 40% of the mice which received huGC33 VLVH showed tumor growth after time of injection.

Huh-7 Luc-GFP cells were injected into NSG mice ($2\times10^6$ cells/head) and after the size of the tumor reached 150-200 $mm^{3,}$ the GPC3 VH-VL CAR-T cells and GPC3 VL-VH CAR-T cells were injected. All mice in a control group which did not receive any injections died after 25 days after the time of injection, while the mice in the groups which received injections of GPC3 CAR-T cells survived at 25 days after injection. Injection of $0.5\times10^6$ cells/head of GPC3VH-VL CAR-T cells showed the tumor size increase and then decrease after day 7 post-injection, while injection of $0.5\times10^6$ cells/head of GPC3 VL-VH CAR-T cells showed the tumor size increase and then decrease after day 7-10 post-injection. Injection of $0.25\times10^6$cells/head show that 20% of mice in the GPC3 VH-VL group showed increase of tumor size, while 40% of mice in the GPC3 VL-VH group showed increase of tumor size (FIG. 11).

Observations for 10 weeks after GPC3 CAR-T injections showed that the group of mice which received injection of GPC3 VL-VH CAR-T cells ($0.25\times10^6$ cells/head) showed 60% survival after day 21 post-injection, and the group which received injection of GPC3 VH-VL CAR-T cells ($0.25\times10^6$ cells/head) showed 80% survival after day 28 post-injection. The group which received GPC3 VL-VH CAR-T cells ($0.5\times10^6$ cells/head) showed 80% survival after day 56 post-injection, and the group which received GPC3 VH-VL CAR-T cells ($0.5\times10^6$cells/head) showed 80% survival after day 66 post-injection.

Figure 12:
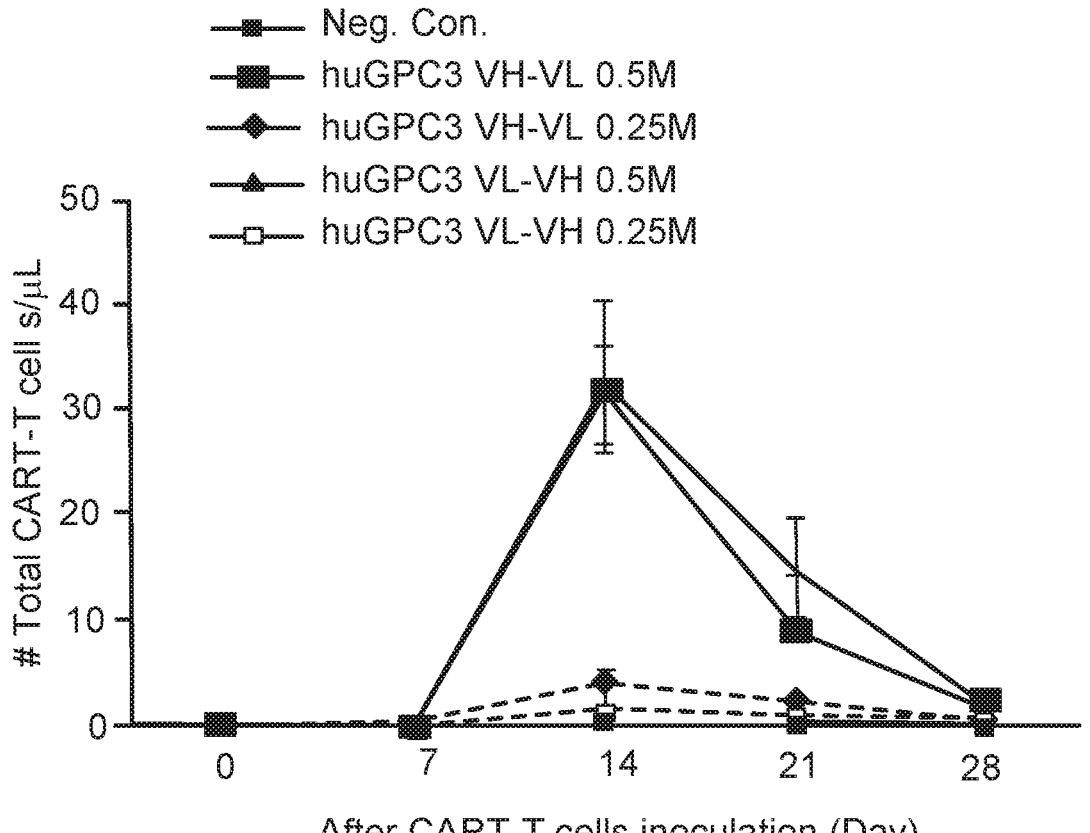
FIG. 12 is a graph showing the change of GPC3 CAR-T cell numbers in the blood of the animals over time after injection of GPC3 CAR-T cell injections. Results show that the number of total CAR-T cells in blood peaked at day 14 after time of injection.

Blood analysis of the mice showed that the number of CAR-T cells in the blood peaked at day 14 post-injection and the results were similar between the two groups (FIG. 12).

These results show that GPC3 VH-VL CAR-T cells were more effective than GPC3 VL-VH CAR-T cells in reducing tumor size while showing higher survival ratings.

---

What is claimed is:

1. An immune cell comprising a chimeric antigen receptor (CAR), wherein the CAR comprises an extracellular antigen-binding domain that binds specifically to glypican-3 (GPC3), a transmembrane domain, and an intracellular signaling domain, wherein the extracellular antigen-binding domain comprises a light chain variable domain represented by SEQ ID NO: 10 and a heavy chain variable domain represented by SEQ ID NO: 8.

2. The immune cell of claim 1, wherein the extracellular antigen-binding domain comprises:

the light chain variable domain comprising a CDR1 comprising SEQ ID NO: 1, a CDR2 comprising SEQ ID NO: 2, and a CDR3 comprising SEQ ID NO: 3; and the heavy chain variable domain comprising a CDRI comprising SEQ ID NO: 4, a CDR2 comprising SEQ ID NO: 5, and a CDR3 comprising SEQ ID NO: 6.

3. The immune cell of claim 1, wherein the antigen-binding domain is humanized.

4. The immune cell of claim 1, wherein the antigen-binding domain is an scFv.

5. The immune cell of claim 1, wherein the transmembrane domain is a transmembrane domain from CD8alpha.

6. The immune cell of claim 1, wherein the intracellular signaling domain comprises an intracellular signaling domain from a protein selected from the group consisting of: 4-1BB/CD137, an activating NK cell receptor, an immunoglobulin protein, B7-H3, BAFFR, BLAME (SLAMF8), BTLA, CD100 (SEMA4D), CD103, CD160 (BY55), CD18, CD 19, CD19a, CD2, CD247, CD27, CD276 (B7-H3), CD28, CD29, CD3 delta, CD3epsilon, CD3gamma, CD3zeta, CD30, CD4, CD40, CD49a, CD49D, CD49f, CD69, CD7, CD84, CD8,CD8alpha, CD8beta, CD96 (Tactile), CD11a, CD11b, CD11c, CD11d, CDS, CEACAM1, CRT AM, a cytokine receptor, DAP-10, DNAM1 (CD226), Fc gamma receptor, GADS, GITR, HVEM (LIGHTR), IA4, ICAM-1, Ig alpha (CD79a), IL-2Rbeta, IL-2R gamma, IL-7R alpha, inducible T cell costimulator (ICOS), an integrin, ITGA4, ITGA6, ITGAD, ITGAE, ITGAL, ITGAM, ITGAX, ITGB2, ITGB7, ITGB1, KIRDS2, LAT, ligand that specifically binds with CD83, LIGHT, LTBR, Ly9 (CD229), Lyl08, lymphocyte function-associated antigen-1(LF A-1), a MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), a Signaling Lymphocytic Activation Molecules (SLAM protein), SLAM (SLAMF1), SLAMF4 (CD244), SLAMF6 (NTB-A), SLAMF7, SLP-76, a TNF receptor protein, TNFR2, TNFSFi4, a Toll ligand receptor, TRANCE/RANKL, VLA1, and VLA-6, or any combination thereof.

7. A method of treating a subject having a glypican-3-associated cancer, the method comprising administering to the subject an immune cell of claim 1.

8. A nucleic acid encoding a chimeric antigen receptor (CAR), wherein the CAR comprises: an extracellular antigen-binding domain that binds specifically to glypican-3 (GPC3), a transmembrane domain, and an intracellular signaling domain, wherein the extracellular antigen-binding domain comprises a light chain variable domain represented by SEQ ID NO: 10 and a heavy chain variable domain represented by SEQ ID NO: 8.

9. The nucleic acid of claim 8, wherein the extracellular antigen-binding domain comprises: the light chain variable domain comprising a CDR1 comprising SEQ ID NO: 1, a CDR2 comprising SEQ ID NO: 2, and a CDR3 comprising SEQ ID NO: 3; and the heavy chain variable domain comprising a CDR1 comprising SEQ ID NO: 4, a CDR2 comprising SEQ ID NO: 5, and a CDR3 comprising SEQ ID NO: 6.

10. A vector comprising the nucleic acid of claim 8.

11. The vector of claim 10 further comprising a promoter operationally linked to the nucleic acid.

12. The vector of claim 11, wherein the promoter is a constitutive promoter.

13. The vector of claim 11, wherein the promoter is an inducible promoter.

14. The vector of claim 10, wherein the vector is a viral vector.

15. The vector of claim 14, wherein the viral vector is a lentiviral vector.

16. A method of producing an engineered immune cell, the method comprising introducing into an immune cell a nucleic acid of claim 8, thereby producing the engineered immune cell.

17. The method of claim 16, further comprising, before the introducing step, obtaining the immune cell from a subject.

18. The method of claim 17, wherein the subject has been diagnosed or identified as having a glypican-3-associated cancer.

19. An engineered immune cell produced by the method of claim 16.

20. A method of treating a glypican-3-associated cancer in a subject, the method comprising administering to the subject an engineered immune cell of claim 19.

21. The method of claim 7, wherein the glypican-3-associated cancer is liver cancer.

22. The method of claim 20, wherein the glypican-3-associated cancer is liver cancer.

* * * * *

SEQUENCE LISTING

<160> NUMBER OF SEQ ID NOS: 16

<210> SEQ ID NO 1
<211> LENGTH: 16
<212> TYPE: PRT
<213> ORGANISM: Artificial Sequence
<220> FEATURE:
<223> OTHER INFORMATION: Light chain CDR1

<400> SEQUENCE: 1

Arg Ser Ser Gln Ser Leu Val His Ser Asn Gly Asn Thr Tyr Leu His
1               5                   10                  15

<210> SEQ ID NO 2
<211> LENGTH: 7
<212> TYPE: PRT
<213> ORGANISM: Artificial Sequence
<220> FEATURE:
<223> OTHER INFORMATION: Light chain CDR2

<400> SEQUENCE: 2

Lys Val Ser Asn Arg Phe Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Light chain CDR3

<400> SEQUENCE: 3

Ser Gln Asn Thr His Val Pro Pro Thr
1               5

<210> SEQ ID NO 4
<211> LENGTH: 5
<212> TYPE: PRT
<213> ORGANISM: Artificial Sequence

```
<220> FEATURE:
<223> OTHER INFORMATION: Heavy chain CDR1

<400> SEQUENCE: 4

Asp Tyr Glu Met His
1               5

<210> SEQ ID NO 5
<211> LENGTH: 17
<212> TYPE: PRT
<213> ORGANISM: Artificial Sequence
<220> FEATURE:
<223> OTHER INFORMATION: Heavy chain CDR2

<400> SEQUENCE: 5

Ala Leu Asp Pro Lys Thr Gly Asp Thr Ala Tyr Ser Gln Lys Phe Lys
1               5                   10                  15

Gly

<210> SEQ ID NO 6
<211> LENGTH: 6
<212> TYPE: PRT
<213> ORGANISM: Artificial Sequence
<220> FEATURE:
<223> OTHER INFORMATION: Heavy chain CDR3

<400> SEQUENCE: 6

Phe Tyr Ser Tyr Thr Tyr
1               5

<210> SEQ ID NO 7
<211> LENGTH: 345
<212> TYPE: DNA
<213> ORGANISM: Artificial Sequence
<220> FEATURE:
<223> OTHER INFORMATION: huGC33 heavy chain variable region

<400> SEQUENCE: 7
caagtgcaac tcgtacaatc aggtgctgaa gtcaaaaagc cgggagcctc tgttaaagtg      60
tcctgtaaag ccagcggcta cacctttacc gattatgaga tgcactgggt tcggcaggct     120
ccgggccaag gtctcgagtg gatcggggct cttgacccaa agacgggcga cacggcttat     180
tcacaaaaat tcaaaggtag ggctactctg actgccgata gtccaccag caccgcgtat      240 atggagctct ctagcttgcg aagcgaggac acggcggtgt actattgcac acgcttctat     300
agttacacat attggggtca aggcacgctt gtgaccgtgt ctagc                     345

<210> SEQ ID NO 8
<211> LENGTH: 115
<212> TYPE: PRT
<213> ORGANISM: Artificial Sequence
<220> FEATURE:
<223> OTHER INFORMATION: huGC33 heavy chain variable region

<400> SEQUENCE: 8

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Ile
        35                  40                  45

Gly Ala Leu Asp Pro Lys Thr Gly Asp Thr Ala Tyr Ser Gln Lys Phe
    50                  55                  60
```

```
Lys Gly Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser
        115

<210> SEQ ID NO 9
<211> LENGTH: 336
<212> TYPE: DNA
<213> ORGANISM: Artificial Sequence
<220> FEATURE:
<223> OTHER INFORMATION: huGC33 light chain variable region

<400> SEQUENCE: 9
gacgtcgtta tgacacagag tcccctctcc ttgccggtga ccctgggtca gcctgcgtcc     60
atctcttgca gatcctccca gtctctggta cactccaacg caacacata cttgcactgg    120 taccaacaaa gacctggtca gtcaccgcga cttctcatat ataaagtttc caataggttc    180
agtggagtgc cagacaggtt cagtggttca ggatcaggca ctgatttcac gcttaaaatc    240
agtcgggttg aggcggagga cgtaggagtt tactattgca gccagaatac gcacgtgccg    300 cctactttg gctctggaac caagttggaa ataaag                              336

<210> SEQ ID NO 10
<211> LENGTH: 112
<212> TYPE: PRT
<213> ORGANISM: Artificial Sequence
<220> FEATURE:
<223> OTHER INFORMATION: huGC33 light chain variable region

<400> SEQUENCE: 10

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Ser Gly Thr Lys Leu Glu Ile Lys
            100                 105                 110

<210> SEQ ID NO 11
<211> LENGTH: 345
<212> TYPE: DNA
<213> ORGANISM: Artificial Sequence
<220> FEATURE:
<223> OTHER INFORMATION: muGC33 heavy chain variable region

<400> SEQUENCE: 11
caggttcaac tgcagcagtc tggggctgag ctggtgaggc ctggggcttc agtgaagctg     60
tcctgcaagg cttcgggcta cacatttact gactatgaaa tgcactgggt gaagcagaca    120
```

-continued

```
cctgtgcatg gcctaaaatg gattggagct cttgatccta aaactggtga tactgcctac      180
agtcagaagt tcaagggcaa ggccacactg actgcagaca atcctccag cacagcctac       240 atggagctcc gcagcctgac atctgaggac tctgccgtct attactgtac aagattctac      300
tcctatactt actggggcca aggactctg gtcactgtct ctgca                      345
```

```
<210> SEQ ID NO 12
<211> LENGTH: 115
<212> TYPE: PRT
<213> ORGANISM: Artificial Sequence
<220> FEATURE:
<223> OTHER INFORMATION: muGC33 heavy chain variable region

<400> SEQUENCE: 12

Gln Val Gln Leu Gln Gln Ser Gly Ala Glu Leu Val Arg Pro Gly Ala
1               5                   10                  15

Ser Val Lys Leu Ser Cys Lys Ala Ser Gly Tyr Thr Phe Thr Asp Tyr
            20                  25                  30

Glu Met His Trp Val Lys Gln Thr Pro Val His Gly Leu Lys Trp Ile
        35                  40                  45

Gly Ala Leu Asp Pro Lys Thr Gly Asp Thr Ala Tyr Ser Gln Lys Phe
    50                  55                  60

Lys Gly Lys Ala Thr Leu Thr Ala Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ala
        115
```

```
<210> SEQ ID NO 13
<211> LENGTH: 336
<212> TYPE: DNA
<213> ORGANISM: Artificial Sequence
<220> FEATURE:
<223> OTHER INFORMATION: muGC33 light chain variable region

<400> SEQUENCE: 13
gatgttgtga tgacccaaac tccactctcc ctgcctgtca gtcttggaga tcaagcctcc       60
atctcttgca gatctagtca gagccttgta cacagtaatg gaaacaccta tttacattgg      120
tacctgcaga agccaggcca gtctccaaag ctcctgatct acaaagtttc caaccgattt      180
tctggggtcc cagacaggtt cagtggcagt ggatcaggga cagatttcac actcaagatc      240
agcagagtgg aggctgagga tctgggagtt tatttctgct ctcaaaatac acatgttcct      300
cctacgttcg gatcggggac caagctggaa ataaaa                              336
```

```
<210> SEQ ID NO 14
<211> LENGTH: 112
<212> TYPE: PRT
<213> ORGANISM: Artificial Sequence
<220> FEATURE:
<223> OTHER INFORMATION: muGC33 light chain variable region

<400> SEQUENCE: 14

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
```

-continued

```
                  20              25              30

Asn Gly Asn Thr Tyr Leu His Trp Tyr Leu Gln Lys Pro Gly Gln Ser
        35              40              45

Pro Lys Leu Leu Ile Tyr Lys Val Ser Asn Arg Phe Ser Gly Val Pro
    50              55              60

Asp Arg Phe Ser Gly Ser Gly Ser Gly Thr Asp Phe Thr Leu Lys Ile
65              70              75              80

Ser Arg Val Glu Ala Glu Asp Leu Gly Val Tyr Phe Cys Ser Gln Asn
            85              90              95

Thr His Val Pro Pro Thr Phe Gly Ser Gly Thr Lys Leu Glu Ile Lys
            100             105             110
```

<210> SEQ ID NO 15
<211> LENGTH: 726
<212> TYPE: DNA
<213> ORGANISM: Artificial Sequence
<220> FEATURE:
<223> OTHER INFORMATION: huGC33         VL-VH

<400> SEQUENCE: 15

```
gacgtcgtta tgacacagag tcccctctcc ttgccggtga ccctgggtca gcctgcgtcc     60
atctcttgca gatcctccca gtctctggta cactccaacg gcaacacata cttgcactgg    120
taccaacaaa gacctggtca gtcaccgcga cttctcatat ataaagtttc aataggttc     180 agtggagtgc cagacaggtt cagtggttca ggatcaggca ctgatttcac gcttaaaatc    240
agtcgggttg aggcggagga cgtaggagtt tactattgca gccagaatac gcacgtgccg    300 cctactttg gctctggaac caagttggaa ataaagggtg gcggcggaag tggtggtggt    360
ggttctgggg gcgggggttc ccaagtgcaa ctcgtacaat caggtgctga gtcaaaaag    420 ccgggagcct ctgttaaagt gtcctgtaaa gccagcggct acacctttac cgattatgag    480
atgcactggg ttcggcaggc tccgggccaa ggtctggagt ggatcggggc tcttgaccca    540
aagacgggcg acacggctta ttcacaaaaa ttcaaaggta gggctactct gactgccgat    600
aagtccacca gcaccgcgta tatggagctc tctagcttgc gaagcgagga cacggcggtg    660
tactattgca cacgcttcta tagttacaca tattggggtc aaggcacgct tgtgaccgtg    720
tctagc                                                               726
```

<210> SEQ ID NO 16
<211> LENGTH: 726
<212> TYPE: DNA
<213> ORGANISM: Artificial Sequence
<220> FEATURE:
<223> OTHER INFORMATION: huGC33         VH-VL

<400> SEQUENCE: 16

```
caagtgcaac tcgtacaatc aggtgctgaa gtcaaaaagc cgggagcctc tgttaaagtg     60
tcctgtaaag ccagcggcta cacctttacc gattatgaga tgcactgggt tcggcaggct    120
ccgggccaag gtctggagtg gatcggggct cttgacccaa agacgggcga cacggcttat    180
tcacaaaaat tcaaaggtag ggctactctg actgccgata agtccaccag caccgcgtat    240
atggagctct ctagcttgcg aagcgaggac acggcggtgt actattgcac acgcttctat    300
agttacacat attggggtca aggcacgctt gtgaccgtgt ctagcggtgg cggcggaagt    360
ggtggtggtg gttctggggg cgggggttcc gacgtcgtta tgacacagag tcccctctcc    420
ttgccggtga ccctgggtca gcctgcgtcc atctcttgca gatcctccca gtctctggta    480
```

-continued

```
cactccaacg gcaacacata cttgcactgg taccaacaaa gacctggtca gtcaccgcga      540
cttctcatat ataaagtttc caataggttc agtggagtgc cagacaggtt cagtggttca      600
ggatcaggca ctgatttcac gcttaaaatc agtcgggttg aggcggagga cgtaggagtt      660
tactattgca gccagaatac gcacgtgccg cctacttttg gctctggaac caagttggaa      720
ataaag                                                                 726
```